(12) United States Patent
Curti et al.

(10) Patent No.: US 8,074,652 B2
(45) Date of Patent: *Dec. 13, 2011

(54) NASAL AND ORAL CANNULA HAVING TWO CAPABILITIES AND METHOD OF PRODUCING SAME

(75) Inventors: James N. Curti, Bakersfield, CA (US); Peter W. Salter, Bakersfield, CA (US)

(73) Assignee: Salter Labs, Arvin, CA (US)

( * ) Notice: Subject to any disclaimer, the term of this patent is extended or adjusted under 35 U.S.C. 154(b) by 139 days.

This patent is subject to a terminal disclaimer.

(21) Appl. No.: 12/510,877

(22) Filed: Jul. 28, 2009

(65) Prior Publication Data

US 2010/0139664 A1    Jun. 10, 2010

Related U.S. Application Data

(62) Division of application No. 11/155,889, filed on Jun. 17, 2005, now Pat. No. 7,565,907.

(51) Int. Cl.
*A61M 11/00* (2006.01)

(52) U.S. Cl. .............. 128/207.18; 264/304; 264/305; 425/275

(58) Field of Classification Search .......... 264/219, 264/221, 301–305, 327, 337, 338; 425/275; 128/204.18, 207.14, 207.18

See application file for complete search history.

(56) References Cited

U.S. PATENT DOCUMENTS

| 2001/0031929 A1 | 10/2001 | O'Toole |
| 2005/0103347 A1 | 5/2005 | Curti et al. |

FOREIGN PATENT DOCUMENTS

| JP | 3-500496 | 2/1991 |
| JP | 7-37730 | 7/1995 |
| WO | 89/09565 | 10/1989 |

*Primary Examiner* — Steven Douglas
(74) *Attorney, Agent, or Firm* — Davis & Bujold, P.L.L.C.

(57) ABSTRACT

A method of forming a cannula from a cannula mandrel assembly comprising a pair of mouthpiece/nasal mandrels and a mating facepiece mandrel. The facepiece mandrel has a pair of conical holes, in an intermediate section thereof, for receiving a leading end of one mouthpiece/nasal mandrel. The conical holes allow the facepiece mandrel to slide along the mouthpiece/nasal mandrels until the conical holes abut with respective mating tapering conical sections and prevent further sliding movement along the mouthpiece/nasal mandrels. Following assembly, the assembly is heated, at least one coating of a polymeric material is applied thereto and heat from the assembly at least partially cures the polymeric material on the assembly. Following curing, the facepiece mandrel and formed cannula are slide along the mouthpiece/nasal mandrels until the facepiece mandrel and formed cannula are removed therefrom. Lastly, the facepiece mandrel is removed from the formed cannula.

20 Claims, 18 Drawing Sheets

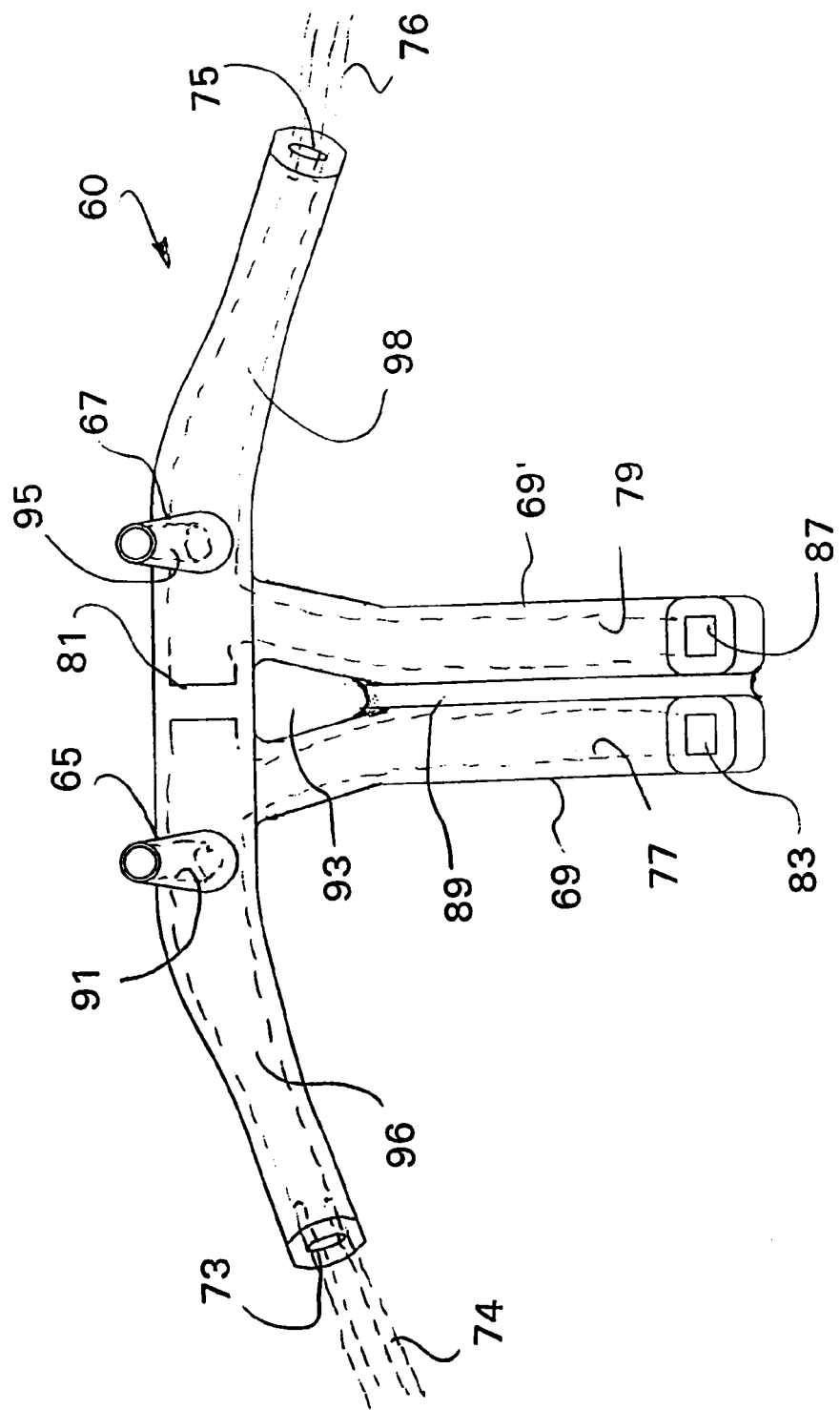

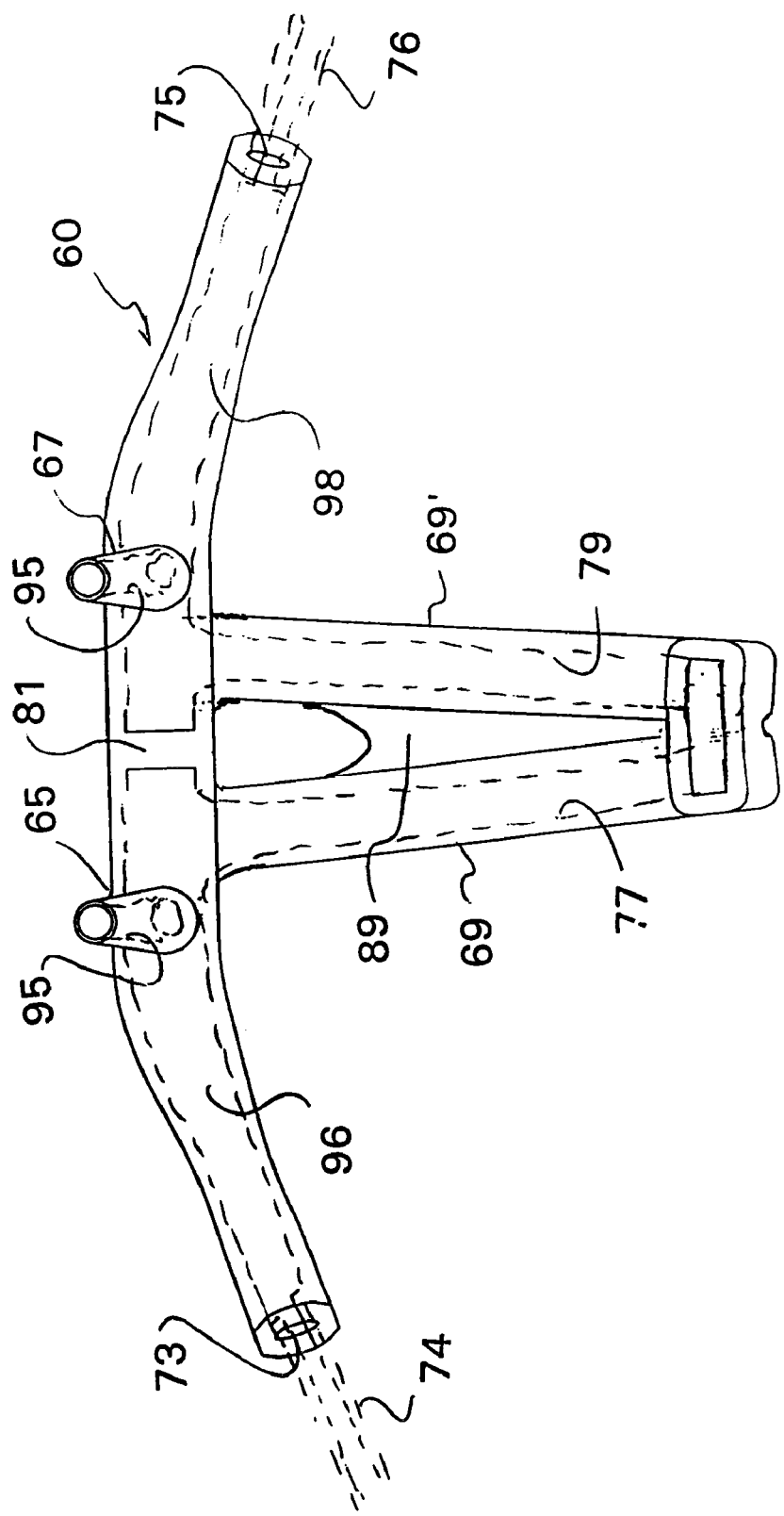

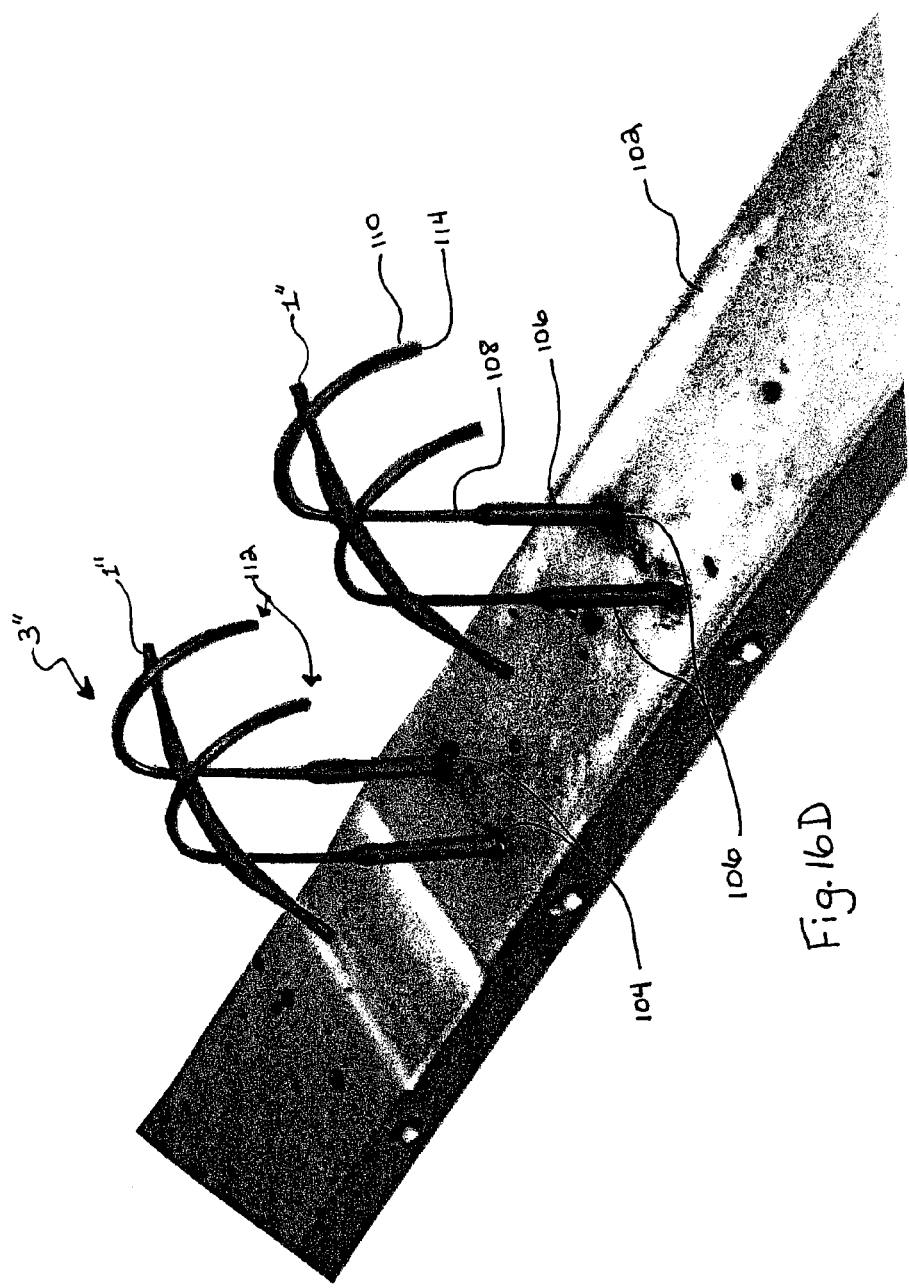

NASAL AND ORAL CANNULA HAVING TWO CAPABILITIES AND METHOD OF PRODUCING SAME

FIELD OF THE INVENTION

This invention relates to a novel cannula which is suitable for use for both nasal and oral applications and a method of producing the cannula using disconnectable mandrel parts to form a mold assembly over or on which the cannula forming plastics or polymeric material is applied to form the cannula.

BACKGROUND OF THE INVENTION

This invention relates generally to cannulas adapted for both oral and nasal applications for monitoring breathing of a patient, sampling the end tidal $CO_2$ content in the exhaled breath of a patient to determine the patient's $CO_2$ blood concentration level, or supplying a treating gas, such as oxygen, to a patient. In addition, the invention relates to a method of manufacturing a cannula adapted to communicate with both nasal passages and the mouth of a patient for use in monitoring breathing, sampling end tidal $CO_2$, supplying a treating gas and is also suitable for the detection of apnea (the absence of breathing).

Nasal cannulas are commonly used to administer a treating gas, such as oxygen, to humans having respiratory problems. Illustrations of nasal cannulas used for this purpose are found in U.S. Pat. No. 3,802,431, for example. Nasal cannulas have also been used for inhalation therapy, made possible by development of inhalation sensors, such as described in U.S. Pat. No. 4,745,925, for example. A nasal cannula can be used to monitor breathing and for detection of apnea when connected to an inhalation sensor.

Nasal cannulas additionally adapted to communicate with the mouth of a patient to permit administration of a gas or sensing of apnea during periods of mouth breathing or nasal blockage are also known.

The present invention relates to a novel cannula and method of manufacturing the novel cannula having the ability to communicate with both nasal cavities as well as the mouth or oral cavity of a patient. This apparatus and method provides, in the preferred embodiment, disconnectable mandrel components which, when assembled with one another, form a mold assembly over which a cannula forming polymeric material is applied, and which, through the capability of each mandrel component being disconnectable from the other mandrel component(s), facilitates removal of the mandrel components from the formed or manufactured cannula.

Prior art relating to dipping of a part in a plastisol to create a coating is exemplified by U.S. Pat. Nos. 3,906,071, 4,695, 241 and 4,800,116, and the disclosures of those references are hereby incorporated by reference.

The closest known prior art is believed to be a sampling cannula sold under the Salter Labs "One—No. 4001 oral/nasal $CO_2$ sample line" trade designation. This cannula has a pair of prongs or sampling line(s) which each communicate with one nostril of the patient and a pair of straight prongs or sampling line(s) which both communicate with the oral or mouth cavity of the patient. A U-shaped wired is glued or otherwise affixed to the exterior surface of the main body of the cannula but the wire extends only about half the length of each of the oral or mouth cavity prongs or sampling line(s) and along the facepiece of the cannula. The wire does not extend along the nares. All of the nasal and the oral prongs or sampling line(s) communicate with an internal passage and thus communicate with one another so that the cannula can only perform one function. The leading free end of the oral or mouth prongs or sampling line(s) can be bent over in front of the teeth of the patient and any excess length of the prong(s) or sampling line(s) can be trimmed, as necessary. This cannula, of Salter Labs, is formed by a cannula mandrel assembly comprising a pair of mouthpiece/nasal mandrels and a facepiece mandrel with an intermediate section of the facepiece mandrel having a pair of spaced apart through holes for each receiving a leading end of one of the mouthpiece/nasal mandrels. Each mouthpiece/nasal mandrel has a first straight section which forms a straight molded mouthpiece and a second straight section which forms a molded nare. A bend is formed in each mouthpiece/nasal mandrel, between the first and second straight sections, to prevent further sliding movement of the facepiece mandrel along the pair of mouthpiece/nasal mandrels.

SUMMARY OF THE INVENTION

It is an object of the invention to provide a method of manufacturing a cannula using an assembly of disconnectable mandrel components over which cannula forming plastics or polymeric material is applied. Application of the plastics or polymeric material over the mandrel assembly and subsequent extraction of the mandrel components from one another, following sufficient curing of the plastics or polymeric material, results in a manufactured cannula with contiguous internal flow paths for sampling the exhaled breath of a patient to detect the end tidal $CO_2$ in the blood of a patient, sensing patient breathing, and/or supplying a treating gas to the patient.

It is a further object of the invention to provide a multi-part mandrel assembly for forming a cannula which facilitates extraction of each of the mandrel assembly components following at least partial curing of the polymeric material forming the cannula.

Still another object of the invention is to form the main body forming mandrel component as two separate, slightly spaced apart components which remain spaced apart from one another by a gap or void, during the dipping or some other polymeric material application process, so that the gap void becomes filled with a plastics or polymeric material to form a wall, septum or barrier which partitions or divides the internal passage of the cannula into two separate compartments or passageways, one which facilitates either sensing of patient breathing, monitoring of the end tidal $CO_2$ in a patient's blood stream or supplying a treating gas to the patient, etc., while the other of which also facilitates another function, such as, sensing of patient breathing, monitoring of the end tidal $CO_2$ in a patient's blood stream, or supplying a treating gas to the patient, etc.

Another object of the invention is to produce a cannula having at least one mouthpiece, and alternatively a pair of side by side mouthpieces, extending from the main body of the cannula to the patient's mouth, the cannula is provided with at least one passageway, or alternatively a pair of separate passageways, for supplying a gas to the patient via a demand regulator for example, or sampling a patient's oral exhalation for monitoring the end tidal $CO_2$ in a patient's blood stream for instance, and the at least one mouthpiece, or alternatively the pair of mouthpieces, has a desired curvature or orientation so that the opening of each mouthpiece is located in or adjacent the mouth or oral cavity of a patient for detecting or sensing the exhaled breath of the patient.

It is a further object of the invention to provide a nasal cannula which is continuously able to both supply and withdraw a gas sample from a mouth of a breathing patient or a patient which alternates breathing between the nose and the mouth and is also able to continuously detect breathing of a patient who alternates breathing between the nose and the mouth.

Yet another object of the invention is to provide a nasal cannula which is relatively inexpensive to manufacture by a dipping process or some other polymeric material application process as a integral unitary cannula.

Still another object of the invention is to provide a multi-part mandrel assembly for forming a cannula which facilitates extraction of each of the mandrel assembly components following at least partial curing the polymeric material forming the cannula.

The invention also relates to a method of forming a cannula comprising the steps of: assembling a cannula mandrel assembly comprising separable engageable parts including a facepiece mandrel and a pair of mouthpiece/nasal mandrels, an intermediate section of the facepiece mandrel being provided with a pair of spaced apart through holes for each receiving a remote free end of one of the mouthpiece/nasal mandrels and allowing the facepiece mandrel to slide along the pair of mouthpiece/nasal mandrels, and each of the mouthpiece/nasal mandrels having a stop feature, with a larger transverse cross section, which prevents further sliding movement of the facepiece mandrel along the pair of mouthpiece/nasal mandrels and while also avoiding flow of a polymeric material between the facepiece mandrel and the mouthpiece/nasal mandrels; heating the cannula mandrel assembly to a desired temperature; providing an uncured polymeric material in flowable state; applying at least one coating of the polymeric material to the cannula mandrel assembly to provide a desired material thickness coating on the cannula mandrel assembly; at least partially curing the coating of the polymeric material on the cannula mandrel assembly to form the cannula; disassembling the cannula mandrel assembly by first sliding both the facepiece mandrel and the formed cannula along the mouthpiece/nasal mandrels toward the free leading ends of the mouthpiece/nasal mandrels until the facepiece mandrel and the partially cured cannula are completely removed from the pair of mouthpiece/nasal mandrels; and then withdrawing the facepiece mandrel from the formed cannula.

The invention also relates to a nasal and oral cannula having a pair of nares and a pair of mouthpieces with a contiguous flow path between the pair of nares and the pair of mouthpieces, the nasal and oral cannula manufactured by the method comprising the steps of: assembling a cannula mandrel assembly comprising separable engageable parts including a facepiece mandrel and a pair of mouthpiece/nasal mandrels, an intermediate section of the facepiece mandrel being provided with a pair of spaced apart conical through holes for each receiving a remote free end of one of the mouthpiece/nasal mandrels and allowing the facepiece mandrel to slide along the pair of mouthpiece/nasal mandrels, and each of the mouthpiece/nasal mandrels having a tapering conical section which forms a stop which prevents further sliding movement of the facepiece mandrel along the pair of mouthpiece/nasal mandrels and while also avoiding flow of a polymeric material between the facepiece mandrel and the mouthpiece/nasal mandrels; heating the cannula mandrel assembly to a desired temperature; providing an uncured polymeric material in flowable state; applying at least one coating of the polymeric material to the cannula mandrel assembly to provide a desired material thickness coating on the cannula mandrel assembly; at least partially curing the coating of the polymeric material on the cannula mandrel assembly to form the cannula; disassembling the cannula mandrel assembly by first sliding both the facepiece mandrel and the formed cannula along the mouthpiece/nasal mandrels toward the free leading ends of the mouthpiece/nasal mandrels until the facepiece mandrel and the partially cured cannula are completely removed from the pair of mouthpiece/nasal mandrels; and then withdrawing the facepiece mandrel from the formed cannula.

The invention further relates to a nasal and oral cannula having first and second nares and first and second curved mouthpieces with a contiguous flow path between the first and second nares and the first and second mouthpieces, the nasal and oral cannula comprising: a main body having opposed end openings and defining a single internal compartment; the first nare, for insertion into a nostril of a patient, being coupled to the main body and communicating with the internal compartment, and the first nare having an inlet/outlet opening at a free end thereof; the second nare, for insertion into a second nostril of the patient and spaced from the first nare, being coupled to the main body and communicating with the internal compartment, and the second nare having an inlet/outlet opening at a free end thereof; the first curved mouthpiece being coupled to the main body and communicating with the internal compartment, and the first mouthpiece having an inlet/outlet opening at a free end thereof; the second curved mouthpiece, spaced from the first mouthpiece, being coupled to the main body and communicating with the internal compartment, and the second mouthpiece having an inlet/outlet opening at a free end thereof; and the curvature of the first and second mouthpieces in combination with an excess length of the first and second mouthpieces results in extra length of the mouthpiece and facilitates trimming of an excess portion of free ends of the first and second mouthpieces so that the openings, of both the first and second mouthpieces, can be aligned substantially normal to an inhalation/exhalation path of the patient and thereby increase the sensitivity of the cannula.

BRIEF DESCRIPTION OF THE DRAWINGS

The invention will now be described, by way of example, with reference to the accompanying drawings, in which:

FIG. 14A is a diagrammatic view of a cannula, manufactured from the mandrel assembly of FIG. 14, having a pair of mouthpieces which are joined with one another along a portion of their lengths but still provided two separate flow passageways;

FIG. 15A is a diagrammatic orthogonal view of a cannula, manufactured from the mandrel assembly of FIG. 15, having a pair of separate mouthpieces and two separate flow passageways;

FIG. 16D is a perspective view following assembly of facepiece mandrels with a pair of combined mouthpiece/nasal mandrels to form two cannula forming assemblies for each forming a cannula;

DETAILED DESCRIPTION OF THE EMBODIMENTS

Figure 1:
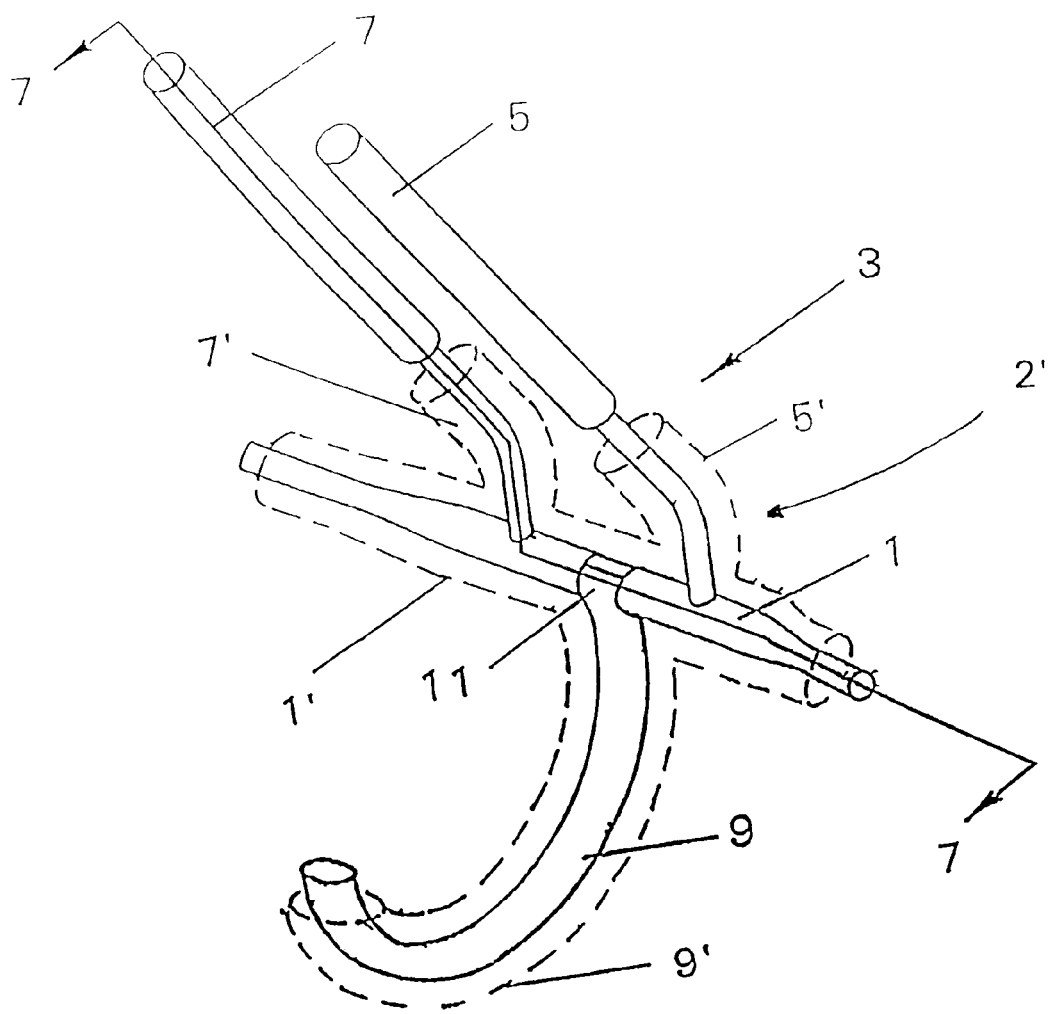
FIG. 1 is an orthogonal view of a cannula mandrel assembly with cannula forming plastics or polymeric material shown in ghost.

Referring to FIG. 1, the main body forming mandrel 1 of a beryllium copper cannula mandrel assembly 3 is shown with a pair of spaced apart nare forming mandrels 5 and 7, and a separate mouthpiece forming mandrel 9 having an end connector 11 for joining the mouthpiece mandrel 9 to the main body forming mandrel 1. A cannula 2', to be formed on the assembly, is shown in ghost and such cannula generally comprises a main body 1', a pair of nares 5', 7' and a mouthpiece 9' which are typically manufactured from polyvinyl chloride (PVC), for example.

Figure 2:
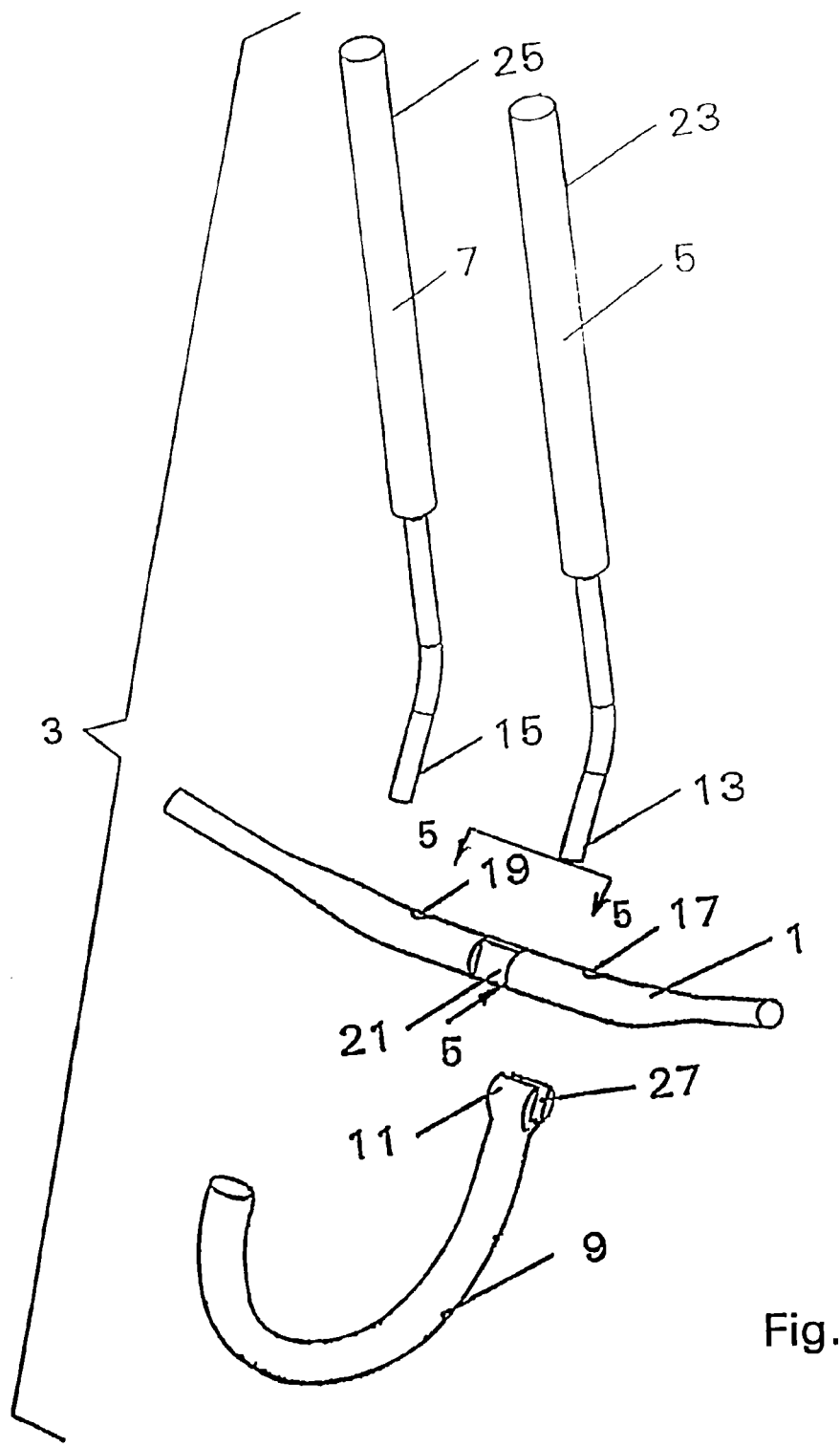
FIG. 2 is an orthogonal view of the cannula mandrel parts prior to assembly.

FIG. 2 shows the mandrel assembly components prior to assembly in order to form or produce the cannula mandrel assembly 3. Each of the nare mandrels 5 and 7 has a reduced diameter section 13 or 15 which form the nares 5', 7', respectively, over which cannula forming plastics or polymeric material is applied. Reduced diameter sections 13 and 15 of the nare mandrels 5 and 7 matingly slide into and are received by respective blind holes 17 and 19 of main body mandrel 1 (see FIG. 5) for releasbly retaining the nare mandrels 5 and 7 therein. Main body mandrel 1 also has a central rectangular recessed section 21 which slidably mates and receives the end connector 11 of the mouthpiece mandrel 9 for releasbly retaining the mouthpiece mandrel 9 therewith.

Nare mandrels 5 and 7 also have enlarged diameter sections 23 and 25 which facilitate support a plurality of identical cannula mandrel assemblies 3 in a jig (not shown) during the molding process. Additionally, the enlarged diameters enable sections 23 and 25 to provide a larger contact surface which allows easier gripping of nare mandrels 5 and 7 to facilitate removal of the nare mandrels 5 and 7 from main body mandrel 1 after partial curing of the PVC, or some other plastisol or plastics, on the cannula mandrel assembly 3.

FIG. 2 further shows the mouthpiece mandrel 9 with the end connector 11 which has a centrally located slot 27 (see FIG. 3) which slidably engages with the rectangular section 21 of the main body mandrel 1. Slot 27 is sized to permit close contact or engagement of the slot 27 with the rectangular section 21 of main body mandrel 1 such that a snug fit or attachment is obtained so as to removably retain the mouthpiece mandrel 9 on the main body mandrel 1 while also facilitating extraction of the mouthpiece mandrel 9 from the rectangular section 21 following partial curing of the PVC, or some other plastisol or plastics material, on the cannula mandrel assembly 3. The outer surface of end connector 11 is sized to approximate a continuation of the outer surface or diameter of main body mandrel 1 to provide a substantially uniform amount of applied PVC, or some other plastisol or plastics material, to an exterior surface of the cannula mandrel assembly 3 while still facilitating withdrawal of the mouthpiece mandrel 9 from the cannula mandrel assembly 3 and the mouthpiece 9' of the manufactured cannula.

Figure 3:
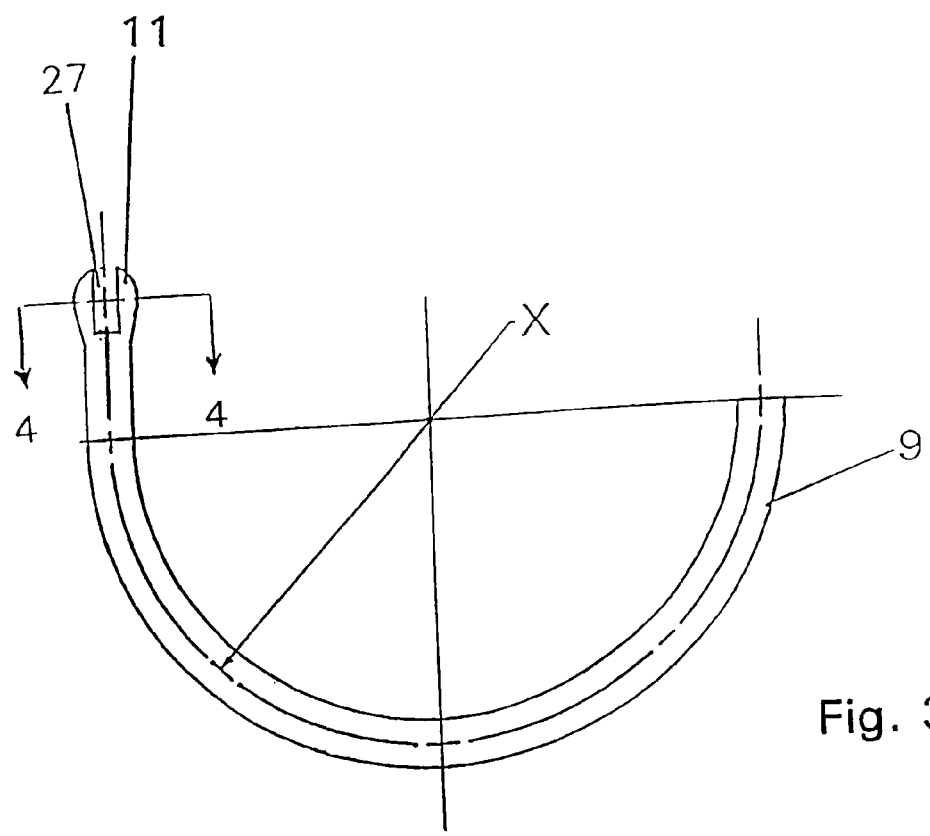
FIG. 3 is a side elevation of the mouthpiece mandrel of FIGS. 1 and 2 showing an end connector.

FIG. 3 shows the general contour of the mouthpiece mandrel 9 having a desired radius X with the end connector 11 located at one end of the mouthpiece mandrel 9 and having a slot 27 formed in the end connector 11. An end of the mouthpiece mandrel 9, adjacent the end connector 11, is generally straight and not curved.

Figure 4:
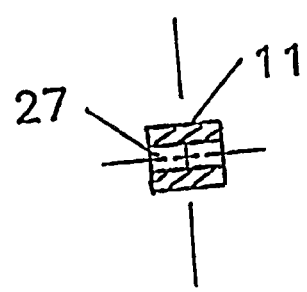
FIG. 4 is an end section of the end connector taken along section line 4-4 of FIG. 3.

FIG. 4 is a view along section line 4-4 of FIG. 3 which shows the shape, e.g., the length, the width, and the thickness, of the end connector 11 and the slot 27.

Figure 5:
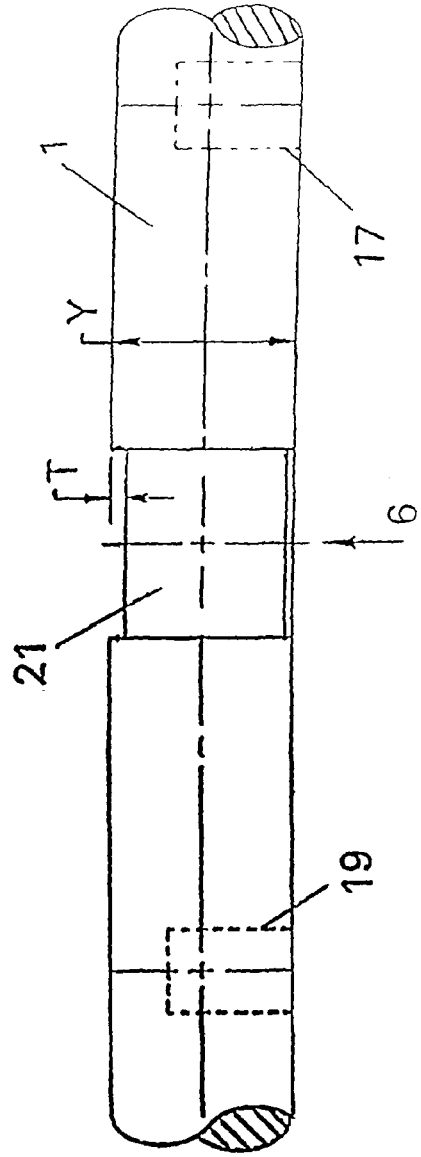
FIG. 5 is a fragmentary side elevation of the main body mandrel of FIGS. 1 and 2 taken along section line 5-5 of FIG. 2.
Figure 6:
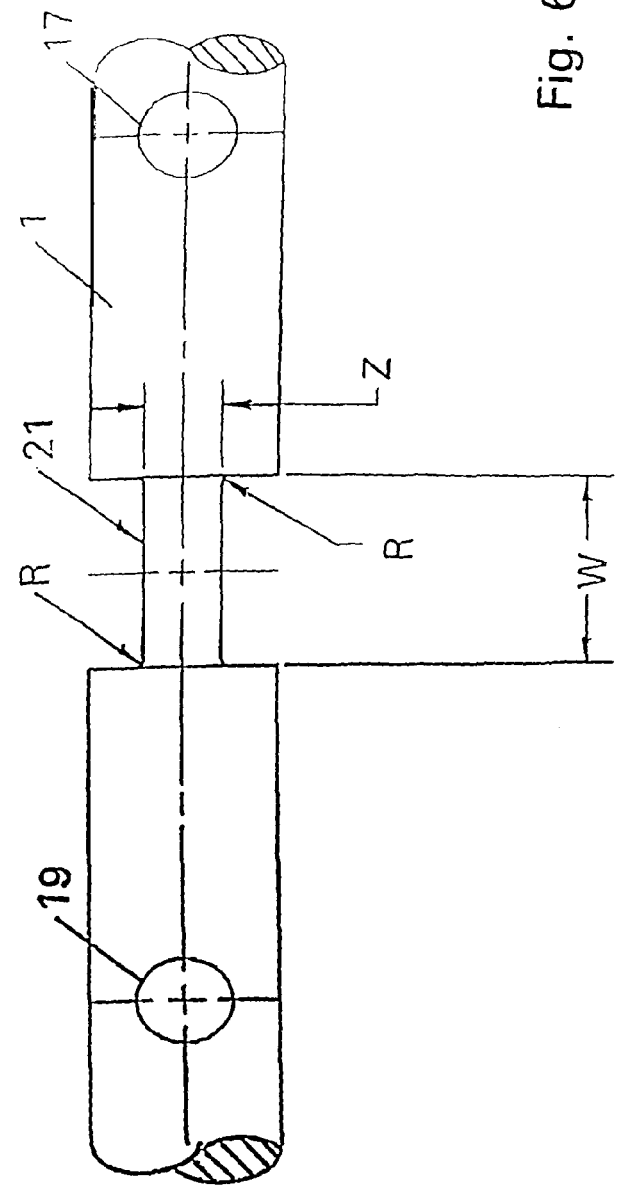
FIG. 6 is an elevation of the main body mandrel taken in the direction of arrow 6 in FIG. 5.

Referring to FIGS. 5 and 6, a pair of spaced apart blind holes 17 and 19 are formed in a central region of the main body mandrel 1. Each blind hole 17 and 19 preferably has a flat or planar bottom surface and is sized to matingly receive, via a sliding fit, one of the reduced diameter sections 13 or 15 of the nare mandrels 5 and 7 in order to engage and releasable support and retain one of the nare mandrels 5 and 7 in a proper molding orientation during application of the PVC, or some other plastisol or plastics material, to the cannula mandrel assembly 3 for formation of the cannula 2'. The rectangular section 21 is made with a shoulder depth T removed to allow the diameter of end connector 11 of mouthpiece mandrel 9 to mate approximately flush with the diameter Y of main body 1.

The rectangular section 21 is shown preferably with a relieving radii R at opposed ends of the section. The relief radius R may be omitted if the main body mandrel 1 is machined or formed in a manner that allows this. Thickness Z of rectangular section 21 permits slot 27 of end connector 11 of mouthpiece mandrel 9 to firmly but slidably mate with rectangular section 21 and adequately maintain the engagement between those two components with one another during dipping or application of the plastics material. Width W of rectangular section 21 is sufficient to closely accommodate end connector 11 of mouthpiece mandrel 9, e.g., a very small clearance fit between those two components is provided.

FIGS. 1 and 2 show nare mandrels 5 and 7 with bend sections 12 and 14. These bend sections 12 and 14 sufficiently curve or direct the nares of the cannula 2', following manufacture of the cannula, so that the nares may be properly aligned and be received within a patient's nasal cavities.

Although beryllium copper is the preferred material for manufacture of the cannula mandrel assembly 3, other materials which possess appropriate working temperature ranges, retain dimensional stability for reuse in a manufacturing environment and will easily and readily release the cannula 2' following partial curing of the PVC, or some other plastisol or plastics material, may be used. Metals including, but not limited to, steel, aluminum, bronze, brass, and copper alloys may be used, as well as some plastics materials. Beryllium copper is preferred due to its ability to transfer heat rapidly and reliably release the cured PVC, plastisol or other plastics material formed on the cannula mandrel assembly 3. Rapid heat transfer is desirable for the material forming the mandrel assembly both during heating of the cannula mandrel assembly 3 and following application of the cannula forming plastics or polymeric material where a partial cure of the plastics or polymeric material is followed by rapid cooling.

Prior to application of a plastics or polymeric solution, such as PVC, the cannula mandrel 3 is coated, usually by a dipping step or spray process, with a silicone release layer or agent to facilitate separation and/or removal of the mandrel components from the plastics or polymeric material to be applied. The application of the plastics or polymeric material, in the preferred embodiment, is by dipping the silicone coated cannula mandrel assembly 3 which has been heated in an oven at an oven temperature of from about 350° F. to about 550° F. (preferably about 450° F.) for about 1 to about 3 minutes prior to dipping in a plastisol solution of PVC. One or more dipping steps may be performed to achieve the desired finished cannula material thickness and each of these dipping steps may be for a duration of 10-30 seconds, for example. During dipping, the mandrel is supported by the outer free enlarged sections 23 and 25 of the nare mandrels.

The use of a plastisol solution, such as PVC, provides a semi-clear finished cannula with sufficient strength to withstand subsequent attachment of various connectors while still being sufficiently flexibility to prevent injury or irritations to the user. Alternatively, other plastics or polymeric materials, which have material properties suitable for this method, capable of forming a plastisol, may be substituted for PVC.

Partial curing of the cannula takes place on the mandrel assembly 3. The cannula mandrel assembly, with the partially cured PVC thereon, is then placed in an oven, for a sufficient time, for further curing at a temperature from about 410° F. to about 450° F. Following curing to stabilize the PVC and after the cannula has sufficiently cooled, the mandrel components are then removed from the manufactured cannula and the release layer or agent assists with such removal, without damaging the cannula. The resulting manufactured nasal cannula has sufficient physical strength and retains its manufactured configuration.

Using the inventive method, a cannula with two nares and a mouthpiece is formed as follows: a cannula mandrel assembly 3 is formed by first, slidably mating and engaging the reduced diameter sections 13 and 15 of nare mandrels 5 and 7 into the blind holes 17 and 19, respectively, of the main body mandrel 1; second, orienting nare mandrels 5 and 7 so that they are properly aligned as shown in FIG. 1; third, slidably mating or engaging the slot 27 of the end connector 11 of the mouthpiece mandrel 9 with the rectangular section 21 of the main body mandrel 1 in a desired orientation relative to the nare mandrels 5 and 7 so that it is also properly aligned as shown in FIG. 1; fourth, supporting the mandrel assembly in a jig and providing a silicone release layer or agent substantially encompassing the mandrel components; fifth, heating the assembled cannula mandrel assembly in an oven at a temperature of from about 350° F. to about 550° F.; sixth, providing a liquid uncured plastisol solution (PVC); seventh, dipping the cannula mandrel assembly into the liquid uncured plastisol solution (PVC), at least once, until the desired material thickness is built-up and/or achieved on the exterior surface of the mandrel assembly 3; eighth, at least partially curing the plastisol (PVC) at a temperature of about 410° F. to about 450° F.; and ninth, following sufficient curing, removing the nare mandrels 5 and 7 from the blind holes 17 and 19 of main body mandrel 1 and the nares 5', 7' by pulling on enlarged diameter sections of the nare mandrels 5 and 7, and removing the mouthpiece mandrel 9 from the mouthpiece 9' by disengaging the slot 27 of the end connector 11 from the rectangular section 21 of the main body mandrel 1 and pulling the mouthpiece mandrel 9 out through the mouthpiece 9'; and finally slidably removing main body mandrel 1 from the main body 1' of the cannula by extracting or withdrawing the same from one end of the manufactured cannula 2'.

Figure 7:
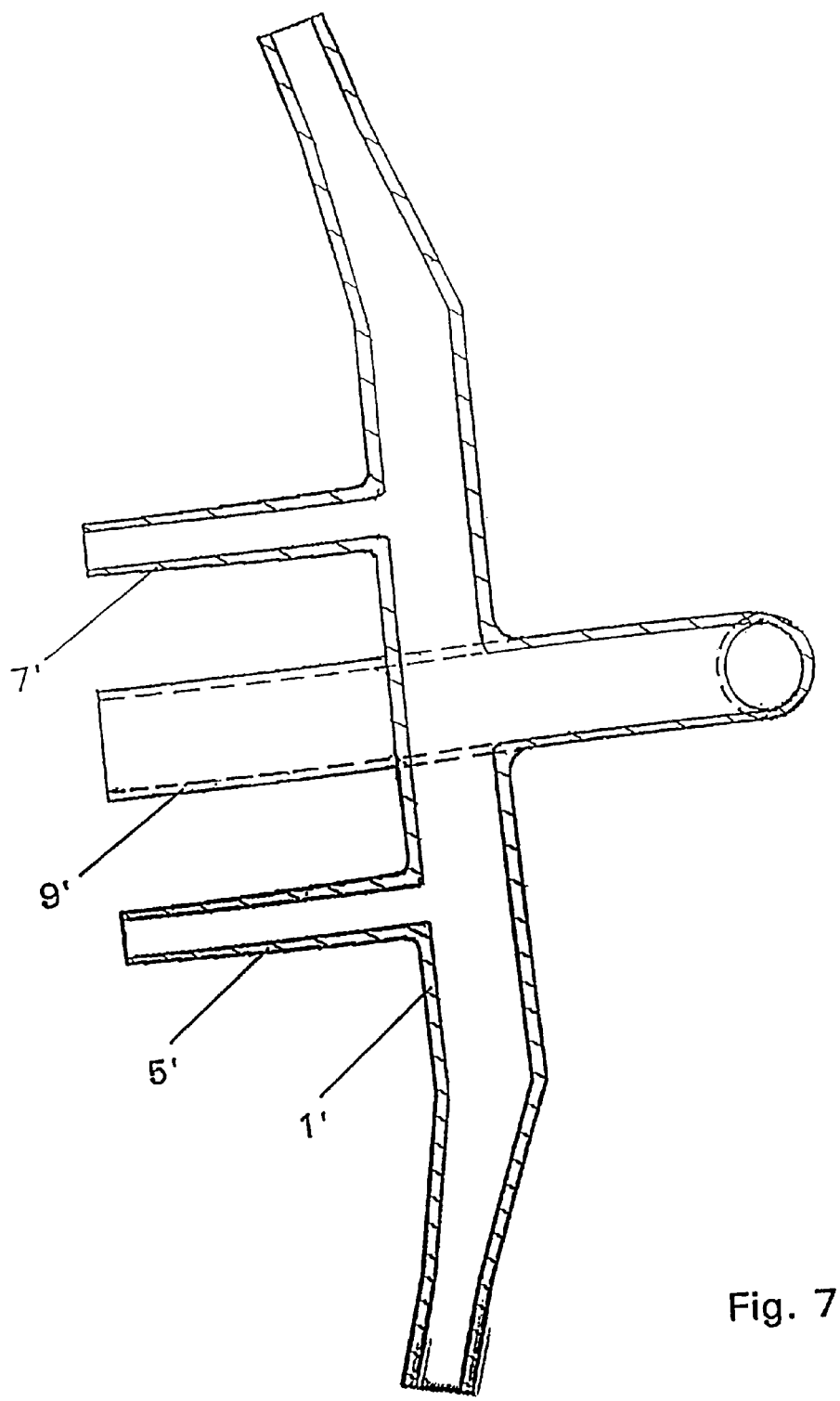
FIG. 7 is a diagrammatic cross-sectional view of a cannula, made by the method of the present invention, taken along section line 7-7 of FIG. 1.
Figure 8:
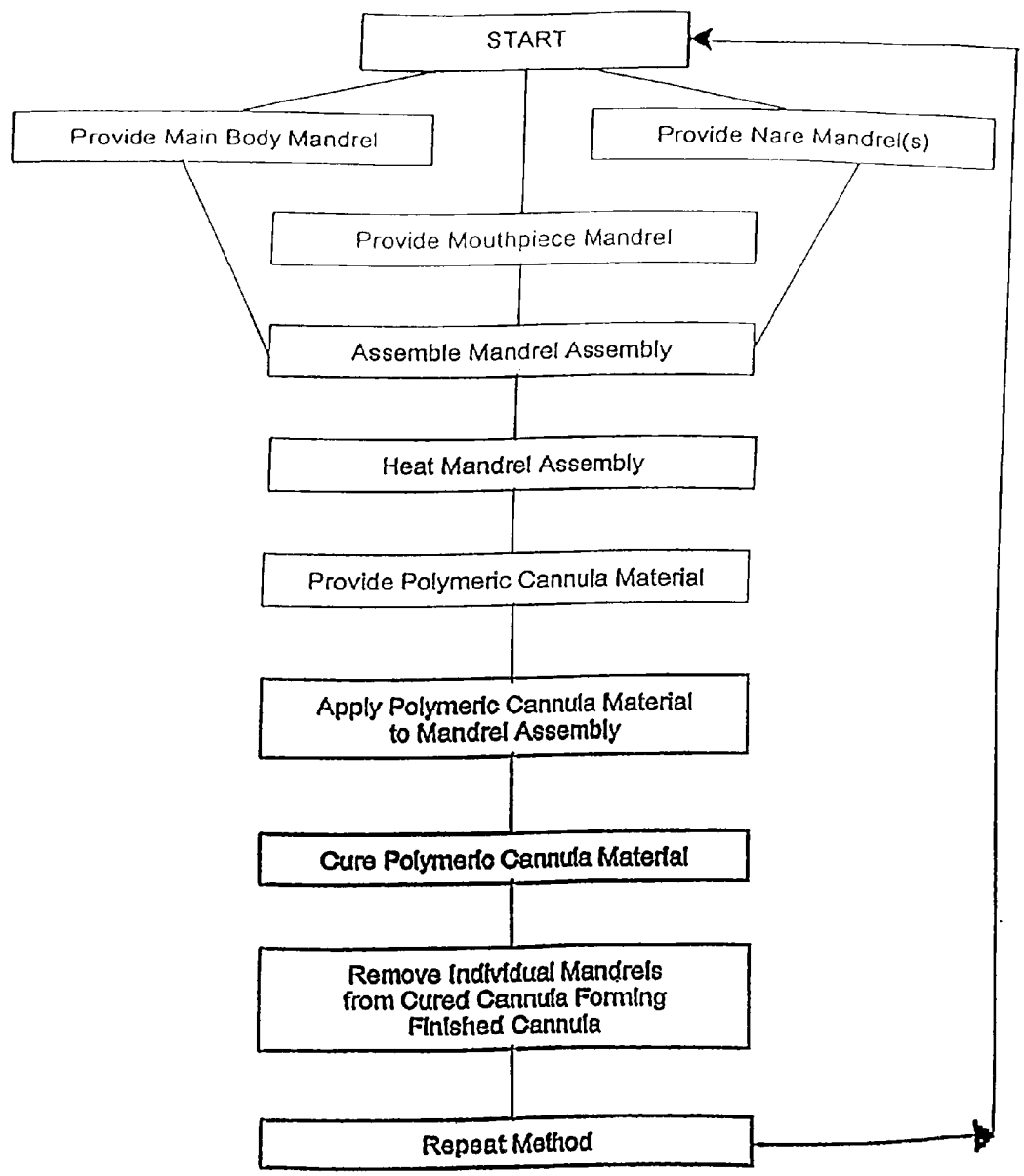
FIG. 8 is a flow diagram of the method of the present invention.
Figure 9:
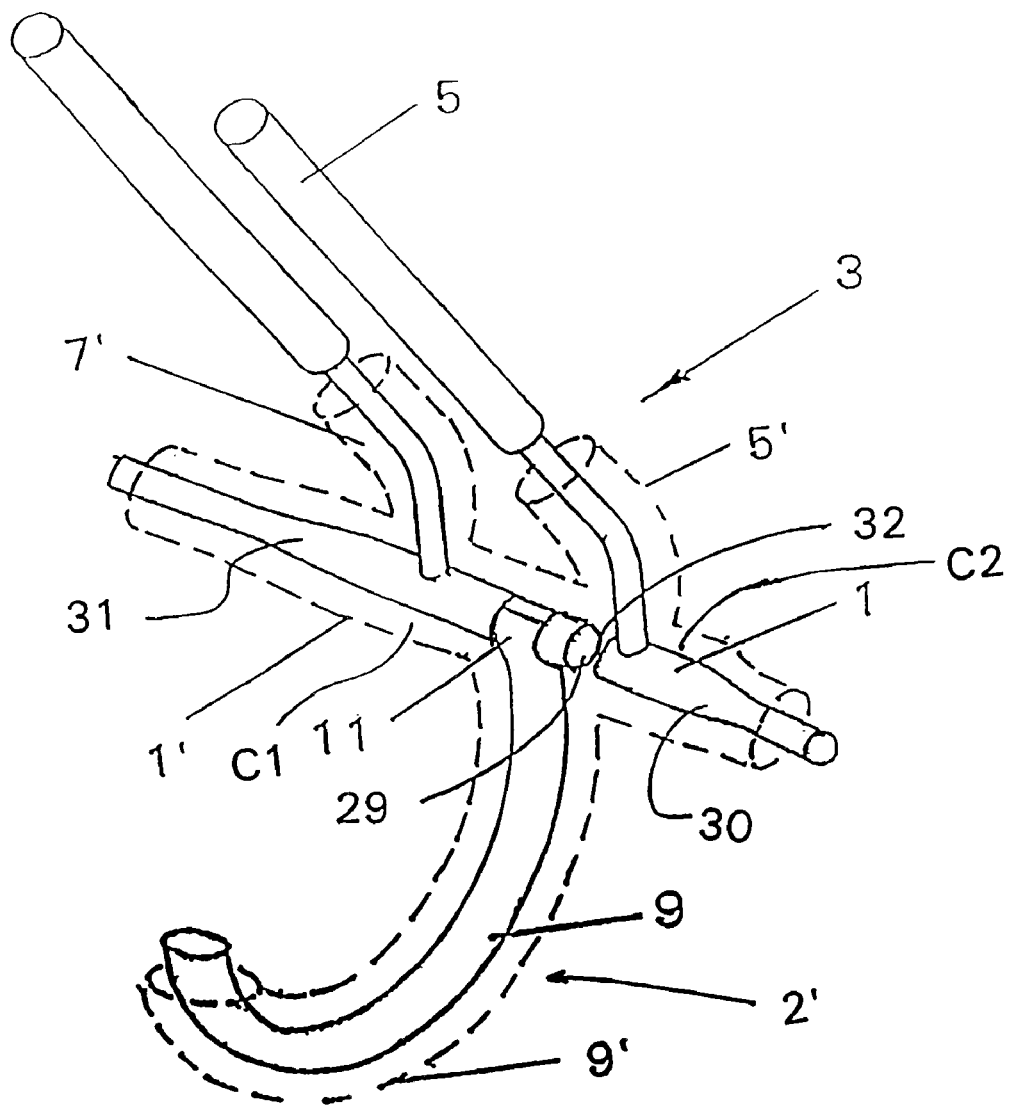
FIG. 9 is an orthogonal view of a cannula mandrel assembly for forming a septum or barrier in a void of the main body forming mandrel, with cannula forming plastics or polymeric material shown in ghost.
Figure 10B:
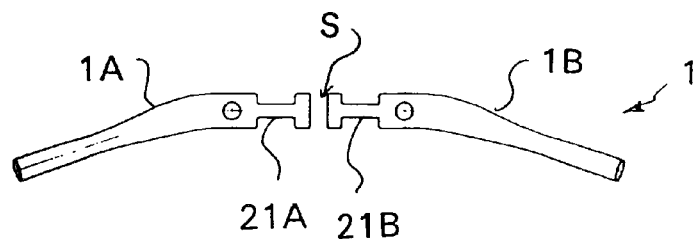
FIG. 10B a front elevational view of only the pair of sections of the main body mandrel.
Figure 10A:
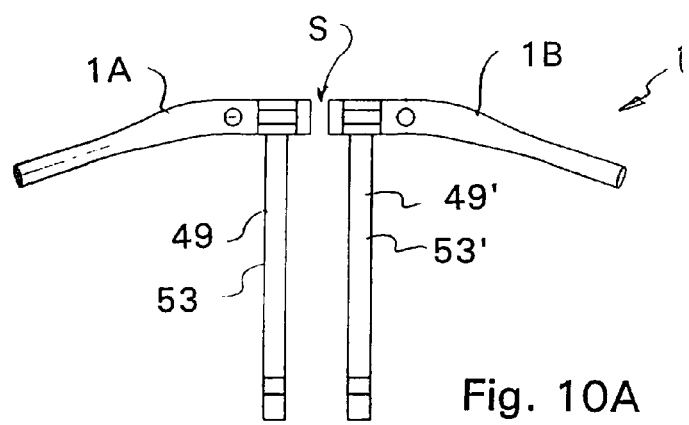
FIG. 10A a front elevational view of another embodiment showing a partially assembled mandrel assembly having the pair of mouthpiece mandrels assembled with the pair of sections of the main body mandrel.
Figure 10C:
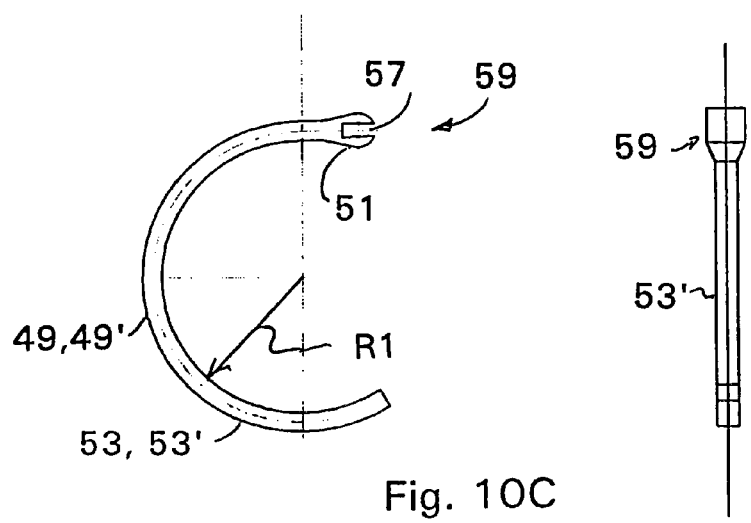
FIG. 10C a side elevational view of one prong for forming the gas flow passageway in the mouthpiece.
Figure 10D:
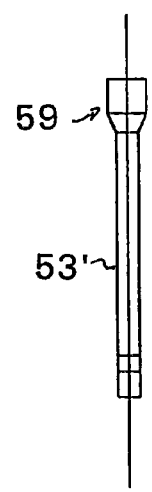
FIG. 10D a front elevational view of the prong of FIG. 10C.

FIG. 7 shows a diagrammatic cross sectional view of a finished or manufactured cannula 2', following removal of the components of the cannula mandrel assembly 3 from the cured PVC cannula, and the formed internal contiguous flow paths through the main body 1', the nares 5' and 7' and the mouthpiece 9' can be seen.

It will be appreciated that the curing step may be completed in two stages, namely, a first partial cure of the PVC produced by the heated cannula mandrel assembly 3 which is sufficient to maintain the PVC on this assembly and a second stage in an oven at the above indicated curing temperatures to complete curing, following the partial curing of the PVC, of the plastisol or some other plastics material.

It will be further appreciated that the opposed outer ends of the main body 1' of the manufactured cannula 2' may be trimmed, as necessary or desired, to provide a discrete area where a flexible connecting tubing or conduit may be connected subsequently thereto, e.g., by solvent bonding with MEK (methyl ethyl ketone) for example, and the mouthpiece 9' may be trimmed to a desired length, prior to use, to suit an individual patient so as to maximize the sensitivity of the finished cannula, e.g., sensing patient breathing, monitoring end tidal $CO_2$ in a patient's blood stream or supplying a treating gas to the patient.

It will also be understood that disassembly of the cannula mandrel assembly 3, following curing of the cannula forming polymeric material, can proceed by removing the mouthpiece mandrel before the nare mandrels as an obvious alternative method step, prior to removal of the main body mandrel.

One modification of the present invention relates to the addition or formation of an internal wall or septum in the internal passage of the cannula 2' to provide an internal partition or barrier therein, e.g., form a "divided cannula." The septum 29 divides the internal chamber C of the main body 1' of the cannula 2' into two completely separate compartments or passageways C1 and C2 so that a first one of the nares 5' can be coupled to a treating gas, such an oxygen source (not shown), to facilitate the supply of supplemental oxygen to one of the nostrils of a patient while the other one of the nares 7' and the central mouthpiece 9' can be coupled to a monitoring device (not shown), such as a transducer, to facilitate monitoring of breathing of the patient or coupled to a demand oxygen conserving device (not shown) while the patient, at the same time, is still able to receive a supplemental supply of oxygen, either continuously or intermittently, during the sensed breathing cycle. Alternatively, one of the nares 5' can be connected to a capnograph, for example, to sample the exhaled breath of a patient and detect the end tidal $CO_2$ in the blood stream of a patient or sensing of patient breathing.

In order to manufacture the septum 29, the main body forming mandrel 1 is formed as first and second separate, slightly spaced apart mandrel components 30, 31 which remain spaced apart from one another, by a small gap or void 32, following assembly of the cannula mandrel assembly 3 and during application of the polymeric material or dipping operation of the manufacturing process so that the void 32 between the first and the second separate, slightly spaced apart mandrel components 30, 31 becomes filled with PVC, or some other plastisol or plastics material, and forms the septum 29. Once the cannula is adequately cured, the septum 29 forms an internal partition or barrier within the main body 1' of the cannula which divides the internal chamber C into two completely separate compartments or passageways C1 and C2.

Following sufficient curing, the nare mandrels 5 and 7 are removed from the blind holes 17 and 19 of main body mandrel 1 and the nares 5', 7' by pulling on enlarged diameter sections of nare mandrels 5 and 7, the mouthpiece mandrel 9 is removed from the mouthpiece 9' by disengaging the slot 27 of the end connector 11 from the rectangular section 21 of the main body mandrel 1 and pulling the mouthpiece mandrel 9 out through the mouthpiece 9'; and the first and second spaced apart components 30, 31 of the main body mandrel 1 are finally removed from the main body 1' of the cannula by pulling the first and second spaced apart components 30, 31 axially away from one another and out from the main body 1' of the cannula 2'. As discussed above, the opposed outer ends of the main body 1' of the manufactured cannula 2' may be trimmed, as necessary or desired, to facilitate connection of a connecting tubing or conduit to each opposed end of the manufactured cannula.

This variation of the manufacturing process is suitable for intermittent nocturnal oxygen delivery even though the patient breaths through his or her mouth or alternates breathing through his or her nose and mouth.

As can be seen in FIGS. 10A-10D and 11, another embodiment of the cannula mandrel assembly 3, for forming a divided cannula having a pair of spaced apart mouthpieces, is shown. For the sake of clarity, the nare mandrels 5 and 7 are not shown attached respectively to the first or the second sections 1A, 1B of the main body forming mandrel 1. The first mouthpiece mandrel 49 comprises a first prong 53 for forming a first gas passageway 77 in the first mouthpiece of the manufactured cannula 60 and the second mouthpiece mandrel 49' comprises a second prong 53' for forming a second gas passageway 79 in the second mouthpiece of the manufactured cannula 60. A further description of the same follows below.

In order to attach both the first and second mouthpiece mandrels 49, 49' to the main body mandrel 1, each of the first and second mouthpiece mandrels 49, 49' include an end connector 51 (see FIG. 10C) attached to a connecting end 59 of the respective first and second prongs 53, 53'. The end connector 51 has a centrally located slot 57 which slidably receives or engages one of the two rectangular sections 21A, 21B (see FIG. 10B) formed in one of the two spaced apart but adjacent body sections 1A, 1B forming the main body mandrel 1, as described above. Each slot 57 is sized to closely contact and engage the respective rectangular section 21A or 21B of main body mandrel 1 of each body section 1A, 1B such that a snug fit and retention of each respective mouthpiece mandrel 49, 49' with the main body mandrel 1 is obtained both prior to and during dipping while still also facilitating removal or extraction of the mouthpiece mandrels 49, 49' from rectangular sections 21A, 21B following sufficient curing and cooling of the PVC, or some other plastisol or plastics material. As with the other embodiments, the outer surface of end connector 51 has a shape, a size and/or a contour which approximates the outer diameter of the main body mandrel 1 to provide a uniform diameter of applied cannula forming polymeric material while also facilitating withdrawal of the mouthpiece mandrels 49, 49' from the mouthpieces 69, 69' of the manufactured cannula 60 (see FIG. 11).

The first and second mouthpiece mandrels 49, 49', once coupled to the main body mandrel 1, extend parallel to but are spaced apart from one another by a small distance, e.g., $\frac{1}{16}$ to $1\frac{1}{2}$ inches or so, more preferably spaced from one another by a distance of about $\frac{1}{4}$ to about 1 inch. The first and second prongs 53, 53' each have a cross sectional area of between about 0.006 and about 0.007 square inches and a radius of curvature R1 of between about 0.5 of an inch to about 2.5 inches or so, and more preferably a radius of curvature of between about 0.75 of an inch to about 1.25 inches or so. The radius of curvature R1 can vary but is generally chosen to facilitate the alignment of the cannula mouthpiece with an opening of the mouth of a patient. The separation between the first and second prongs 53, 53', according to this embodiment, forms a uniform elongate spacing or area between those two prongs so that a sufficient space is provided during the dipping operation(s), which applies a plastisol coating to the cannula mandrel assembly 3 and each of the first and second prongs 53, 53' without any plastisol interconnecting or joining the two mouthpieces 69, 69' with one another. As a result of this, the two mouthpieces 69, 69' are completely separate and movable independent of one another following formation of the cannula 60.

The transverse cross sectional area D (see FIG. 11) of the openings 83, 87 and the internal gas flow passageway 77, 79 within the mouthpiece 69, 69' of the cannula, once the first and second prongs 53, 53' are removed therefrom, are sufficiently sized for supplying a desired treating gas to a patient, for example, via a demand regulator to a mouth breathing patient. Alternatively, the respective internal gas flow passageway within the mouthpiece 69, 69' of the cannula is sufficiently sized to allow withdrawal, detection, sampling, etc., of an exhalation gas(es) from a mouth of a breathing patient. It is to be appreciated that the transverse cross sectional area of the internal gas flow passageway, formed in the mouthpiece 69, 69', for supplying a treating gas to a patient may typically be larger than the transverse cross sectional area of a gas flow passageway for withdrawing or sampling a gas(es) from a patient. If desired, a first and/or second prong 53, 53' with a larger or smaller transverse cross sectional area, to thereby define a correspondingly larger or smaller internal gas flow passageway(s) 77 and/or 79 in either or both the first and the second mouthpieces 69, 69', could be utilized. But, for the sake of simplicity of manufacture and for added versatility, the transverse cross sectional areas of both of the formed internal gas flow passageways 77, 79 in the first and second mouthpieces 69, 69' can be manufactured identical to one another.

Figure 11:
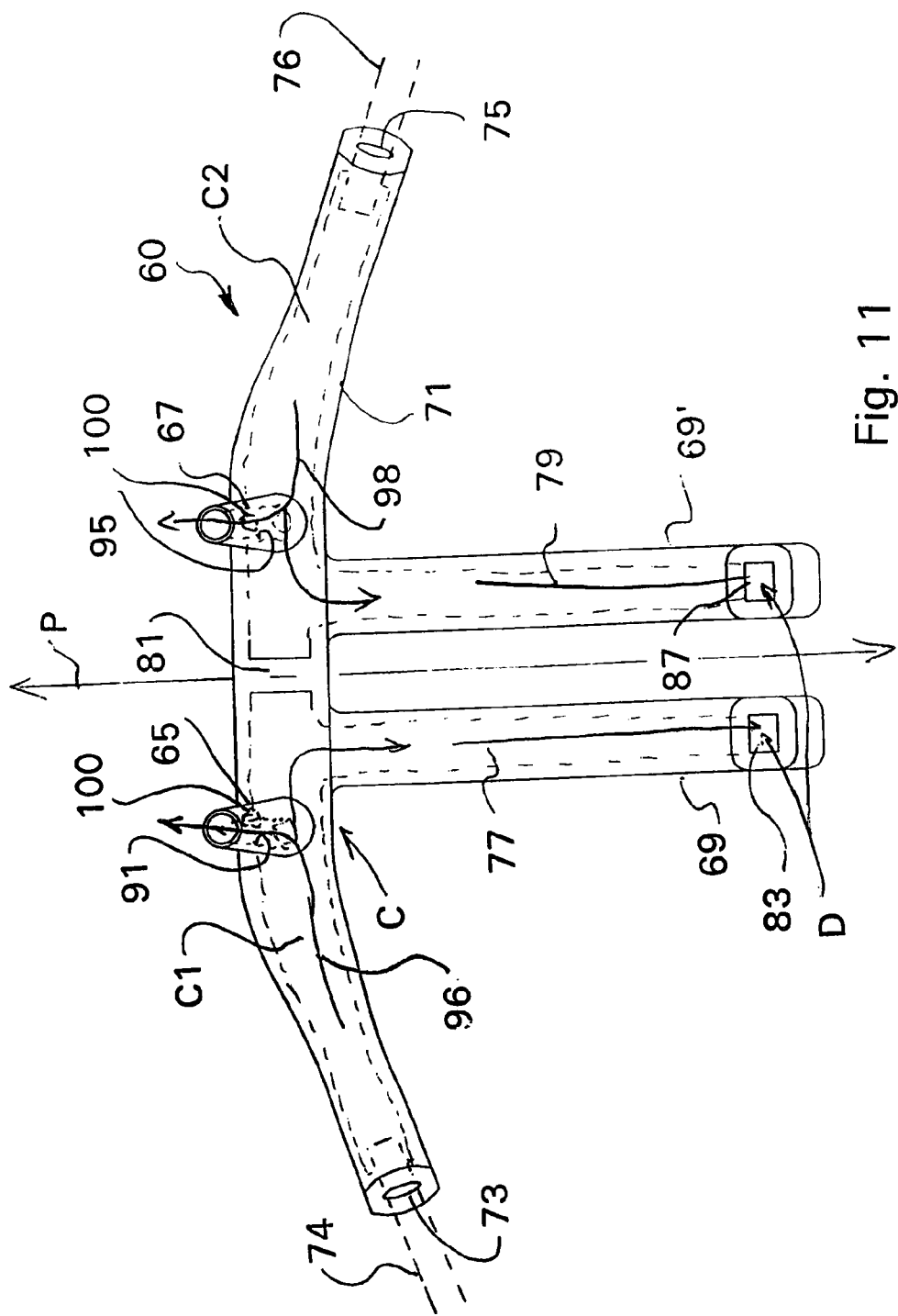
FIG. 11 is a diagrammatic orthogonal view of a cannula, manufactured from the mandrel assembly of FIG. 10, having a pair of separate mouthpieces and two separate flow passageways.

The above described first and second mouthpiece mandrels 49, 49' are each assembled with one of the body sections 1A or 1B of the main body mandrel 1 and one of the first and second nare mandrels 5, 7 to form the cannula mandrel assembly 3. Before dipping or application of the polymeric material, the cannula mandrel assembly 3 is sprayed or otherwise coated with a release film, layer or agent and preheated to a desired temperature and then dipped in or otherwise applied with the cannula forming polymeric plastisol to provide a desired thickness or layer of a partially cured plastics or polymeric material on the exterior surface of the cannula mandrel assembly 3 and thereby form a manufactured plastisol cannula. The partially cured manufactured plastisol cannula is then heated in an oven to further cure the plastics or polymeric material, as previously described. After sufficient curing of the plastics or polymeric material, both of the first and second nare forming mandrels 5, 7, the first and second mouthpiece forming mandrels 49, 49' and the first and second sections 1A, 1B of the main body forming mandrels 1 are extracted or removed from the cured polymeric material and the remaining cured structure results in the manufactured and cured cannula 60, as shown in FIG. 11. If desired or necessary, the end of the cannula 60 can be trimmed to a desired length.

The manufactured cannula 60, formed from the above described process and cannula mandrel assembly 3 shown in FIGS. 10A-10D, after addition of the nare mandrels 5 and 7, comprises a main body 71 with a pair of opposed internal chamber end openings 73, 75 located at opposite ends of the main body 71 for coupling, by an adhesive such as MEK for example, each opposed end of the cannula 60 to a flexible gas delivery, pressure detecting or gas sampling tubing or some other conduit 74, 76 (only partially shown in FIG. 11). The gap or spacing formed between the adjacent ends of the first and second sections 1A, 1B of the main body forming mandrel 1 (see FIGS. 10A and 10B) creates a partition, a wall, a dividing member or a septum 81 which divides the internal chamber C into a first compartment or passageway C1 and a completely separate second compartment or passageway C2. The first compartment or passageway C1 communicates with the first chamber end opening 73 while the second separate compartment or passageway C2 communicates with the second chamber end opening 75. A first fluid passageway 91, formed in the first centrally located nare 65, communicates with the first compartment or passageway C1 while a second fluid passageway 95, formed in a second centrally located nare 67, communicates with the second separate compartment or passageway C2. The first gas passageway 77, formed in the first mouthpiece 69, communicates with the first compartment or passageway C1 while the second gas flow passageway 79, formed in the second mouthpiece 69', communicates with the second separate compartment or passageway C2. The pair of centrally located but spaced apart nares 65, 67 of the cannula are located for insertion into the nostrils of a patient's nose while the first and second centrally located mouthpieces 69, 69' of the cannula are located substantially adjacent the middle section of the main body 71, between the nares 65, 67, for communication with the mouth of the patient.

Figure 11A:
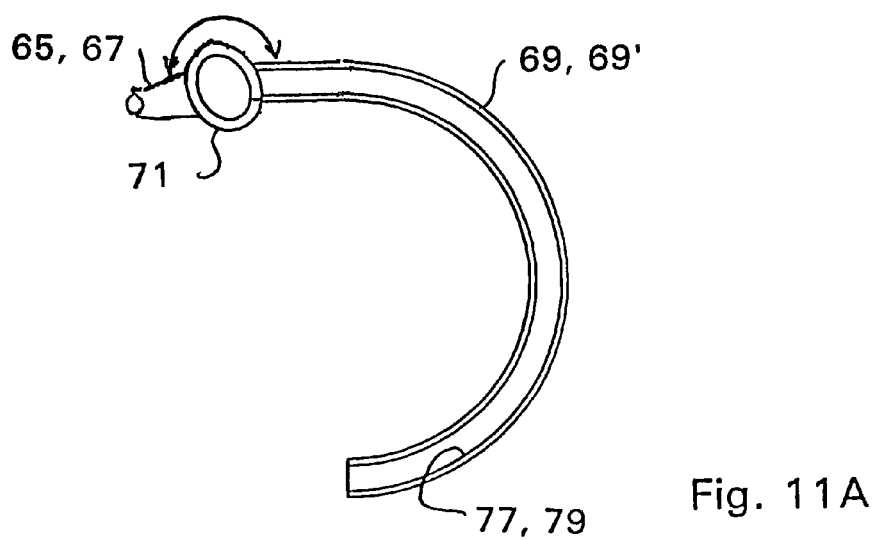
FIG. 11A is a diagrammatic side elevational view of a cannula of FIG. 11.

As best seen in FIG. 11A, the first and second mouthpieces 69, 69' of the nasal cannula 60 are shown in their originally molded shape or configuration which generally corresponds to the curvature of the mouthpiece mandrel 49. As can be appreciated, due to the nature of the resiliency of the plastisol material from which the cannula 60 is formed, the first and second mouthpieces 69, 69' will generally retain and/or return back to such originally molded curvature. As discussed above, the mouthpiece 69, 69' may be trimmed to a desired length (shown in dashed lines in FIG. 12B) to suited an individual patient so as to maximize the sensitivity of the cannula, e.g., sensing patient breathing, monitoring end tidal $CO_2$ in a patient's blood stream, supplying a treating gas to the patient, detecting sleep apnea, etc. That is, the gas passage openings 83 and 87 are generally aligned with, e.g., extends substantially perpendicular to, the exhalation/inhalation path E of the patient.

It is to be appreciated that the nasal cannula 60 is a unitary structure which comprises two completely separate internal flow paths 96 and 98. Each one of the two completely separate internal flow paths 96 and 98 is suitable for supplying a treating gas to a patient both via a nostril and the mouth of a patient as well as capable of withdrawing or sampling an exhalation gas(es) from the patient, or monitoring breathing characteristics, detecting pressure, etc. The first compartment or passageway C1, of the internal chamber C of the main body of the cannula 60, is in constant and continuous communication with the first gas passageway 77 of the first mouthpiece 69 and also in constant and continuous communication with the first gas passageway 91 in the first nare 65 and with the first chamber end opening 73 and all of these components and passageways form the first completely separate internal flow path 96. The second compartment or passageway C2, of the internal chamber C of the main body of the cannula 60, is in constant and continuous communication with the second gas passageway 79 of the second mouthpiece 69' and also in constant and continuous communication with the second gas passageway 95 in the second nare 67 and with the second chamber end opening 75 and all of these components and passageways form the second completely separate internal flow path 98. As a result of these completely separate fluid passageways 96, 98, each completely separate fluid passageway 96 or 98 can facilitate preforming one of the following functions: monitor breathing of a patient via the mouth and/or the nose, sampling the end tidal $CO_2$ content in the exhaled breath of a patient via the mouth and/or the nose to determine the patient's $CO_2$ concentration level in the blood, supplying a treating gas to a patient via the mouth and/or the nose, detecting apnea via the mouth and/or the nose, etc. If desired, the septum 81 may be eliminated so that the first and second compartments or passageways C1 and C2, the first and second internal gas passageways 77, 79 and the first and second gas passageways 91 and 95 in the nares 65 and 67 are all in constant and continuous communication with one another.

It is to be appreciated that it is not necessary to have the two mouthpieces 69, 69' precisely centered between the nares 65, 67. It is conceivable that the mouthpieces could be located on one side or the other of a central plane P bisecting a center of main body 71 into two halves. It is to be appreciated further that it is not necessary to have the septum 81 center within the main body as long as the septum 81 is generally located between the nares 65, 67 and the first and second mouthpieces 69, 69'. Also, as set forth in U.S. Pat. No. 6,439,234 to Curti et al., the disclosure of which is hereby incorporated by reference, additional openings 100 (shown as dashed lines in FIG. 11), preferably adjacent the remote free end of each nare, could be provided in the nares 65, 67 and possibly in the gas passageway 69, 69' of the mouthpiece to prevent occlusion of the nares 65, 67 and facilitate monitoring, detecting, sampling, delivery, etc.

As can be seen in FIG. 11A for example, the first end of the nares 65 and 67 generally form an angle of between about 180° or so ±5 degrees with the coupled end of the mouthpieces 69, 69'.

Figure 12A:
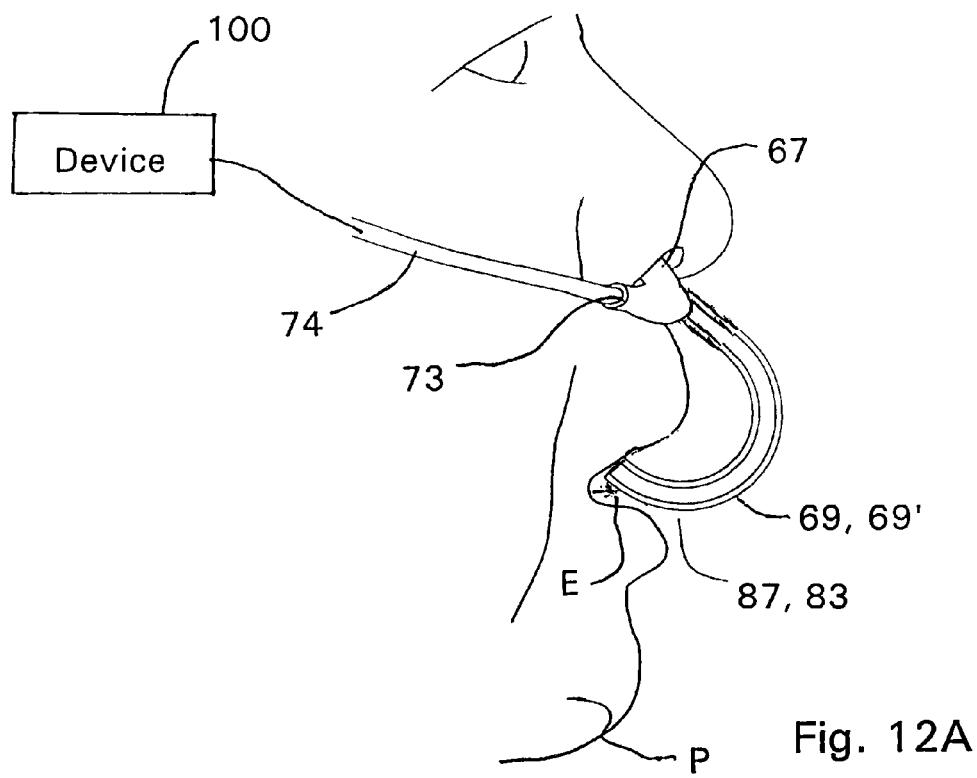
FIG. 12A is a side elevational views showing the originally molded orientation of the mouthpiece relative to an open mouth of a patient.
Figure 12B:
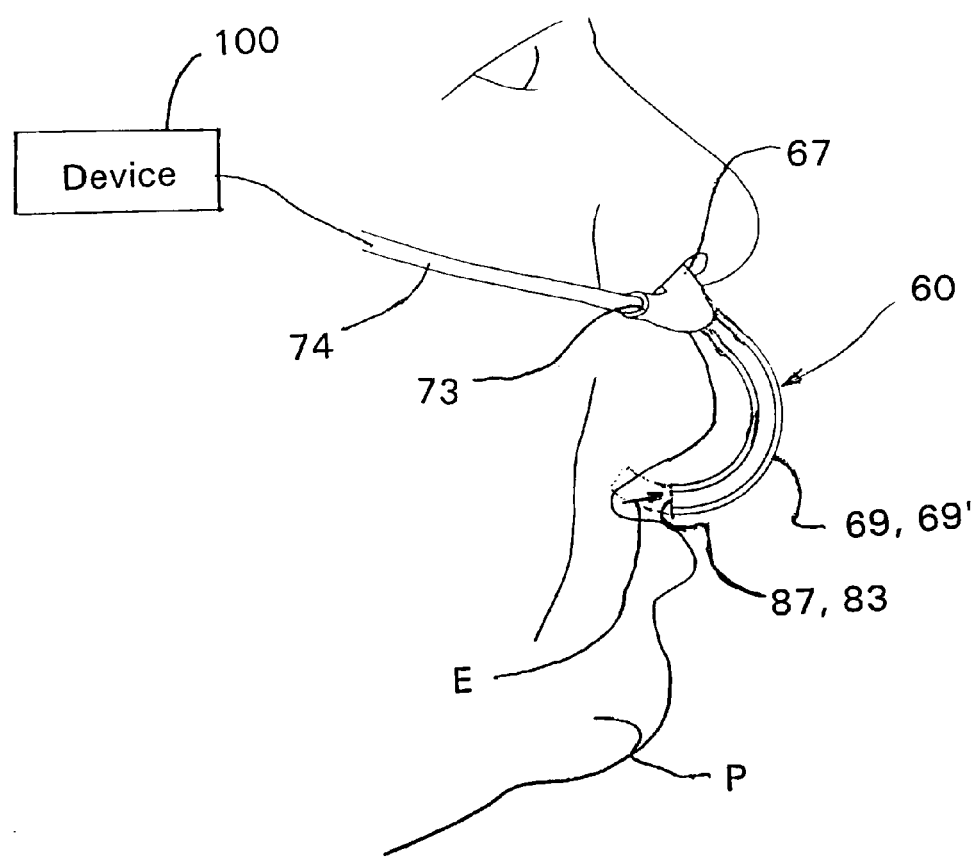
FIG. 12B is a side elevational view showing the trimmed orientation of the mouthpiece, relative to an open mouth of a patient, for aligning an opening of the mouthpiece with the patient's oral inhalation/exhalation path.

FIG. 12A shows a typical orientation of the mouthpieces 69, 69', relative to an open position of a patient's mouth following initial installation of the cannula on the patient. As can be readily observed in FIG. 12A, it is possible that the gas passage openings 83 and 87 may not initially be precisely aligned with the exhalation/inhalation path E of the patient, e.g., the plane defined by the gas passage openings 83 and 87 may not extend substantially normal to the exhalation/inhalation path E of the patient as her or she breaths normally. The remote free end of the mouthpieces 69, 69' can be cut or trimmed, as necessary (see FIG. 12B in which the removed or trimmed portion of the mouthpieces 69, 69' is shown in dashed lines), so that thereafter a plane defined by the openings to the internal gas passageways 77, 79 of the mouthpieces 69, 69' will lie substantially normal to the exhalation/inhalation path E of the patient. Such alignment of the openings 83 and 87 to the internal gas passageways 77, 79 of the mouthpieces 69, 69' assists with better collection of a gas sample(s), more accurate detection of an exhalation pressure, more accurate delivery of a gas(es), more accurate monitoring of the patient's breathing, etc. The above described arrangement permits minor adjustment of the configuration and/or orientation of the mouthpieces 69, 69' prior to use.

Figure 13A:
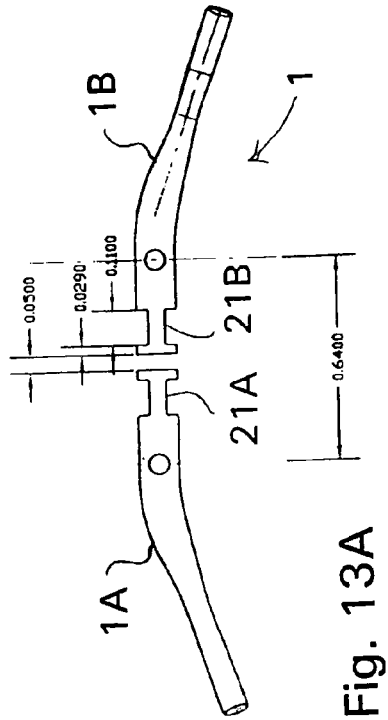
FIG. 13A a front elevational view of only the pair of sections of the main body mandrel.
Figure 13B:
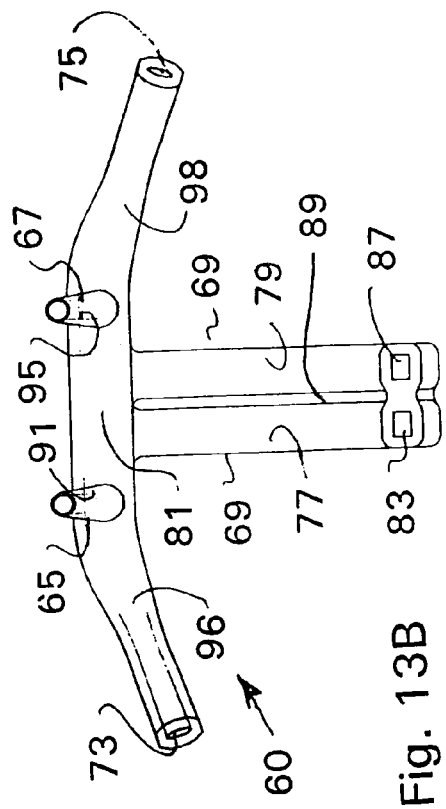
FIG. 13B is a diagrammatic view of a cannula, manufactured from the mandrel assembly of FIG. 13A, having a pair of mouthpieces which are joined with one another along their entire lengths but still provided two separate flow passageways.
Figure 13:
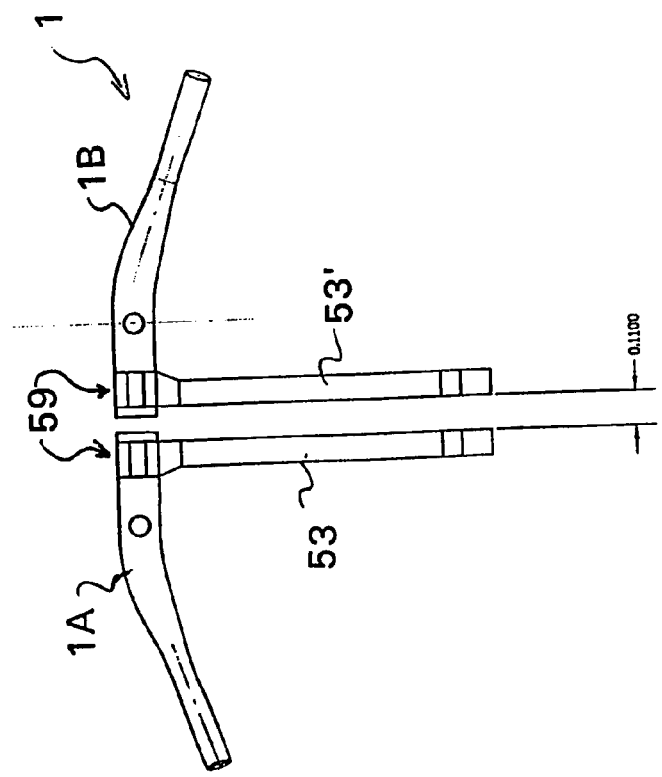
FIG. 13 a front elevational view of a further embodiment showing a partially assembled mandrel assembly having the pair of mouthpiece mandrels assembled with the pair of sections of the main body mandrel.

With reference to FIGS. 13 and 13A, another embodiment of the cannula mandrel assembly will now be discussed. For the sake of clarity, the nare mandrels are not shown attached respectively to the first or the second sections 1A, 1B of the main body forming mandrel 1 in FIG. 13. As this embodiment is similar to the previous embodiments, identical reference numerals are given to identical elements and only the differences between this embodiment and the embodiment of FIGS. 10A-10D, in particular, will be discussed in detail.

The principal difference between this embodiment and the embodiment of FIGS. 10A-10D is that the rectangular sections 21A and 21B are located slightly closer to one another so the first and second prongs 53, 53', when engaged therewith, are mounted in a closer relationship to one another. That is, each rectangular section 21A and 21B is located about 0.0290 inches of so from an end of either the first or the second sections 1A, 1B of the main body forming mandrel 1 and so that adjacent edges of the first or the second sections 1A, 1B are spaced from one another by a distance of about 0.050 inches. This results in the first and second prongs 53, 53', when engaged with the respective rectangular sections 21A, 21B, being spaced or separated from one another by only a distance of about 0.1100 inches or so.

The net result of this modification occurs during the dipping process or application of the polymeric material. That is, during the dipping process or application of the polymeric material, the first and second prongs 53, 53' are located sufficiently closed to one another such that the plastisol at least partially fills the space or gap located between the first and second prongs 53, 53' and forms an interconnecting web 89 and well as encases and surrounds each one of the first and second prongs 53, 53' to form an integral mouthpiece comprising a pair of joined or interconnected mouthpieces 69, 69' (see FIG. 13A) which move in unison with one another. In all other respects, this embodiment is substantially identical to the embodiment of FIGS. 10A-10D, 11 and 11A.

Figure 14:
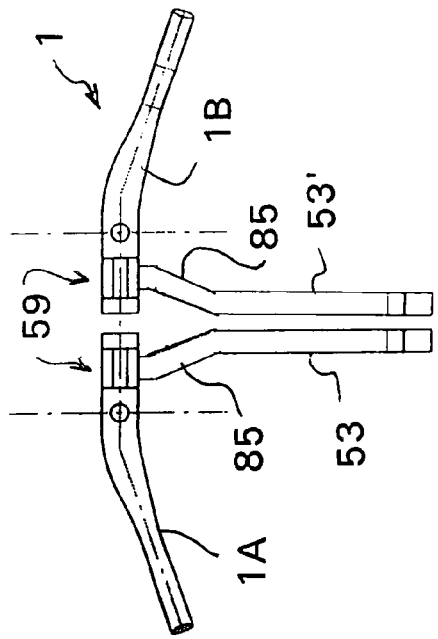
FIG. 14 a front elevational view of still another embodiment showing a partially assembled mandrel assembly having the pair of mouthpiece mandrels assembled with the pair of sections of the main body mandrel.

With reference to FIGS. 14 and 14A, another embodiment of the cannula mandrel assembly will now be discussed. For the sake of clarity, the nare mandrels are not shown attached respectively to the first or the second sections 1A, 1B of the main body forming mandrel 1 in FIG. 14. As this embodiment is similar to the previous embodiments, identical reference numerals are given to identical elements and only the differences between this embodiment and the embodiment of FIGS. 10A-10D, in particular, will be discussed in detail.

The principal difference between this embodiment and the embodiment of FIGS. 10A-10D is that each one of the first and second prongs 53, 53' has a small inwardly directed bend or transition 85 formed adjacent the connecting end 59 of the respective first and second prongs 53, 53'. As a result of this small inwardly directed bend or transition 85 toward one another, when the first and second prongs 53, 53' are engaged with the respective first and second sections 1A, 1B, the connecting ends 59 are located further away from one another while the remote free ends of the first and second prongs 53, 53' are located in a closer spaced relationship to one another. That is, the connecting ends 59 of the first and second prongs 53, 53' are spaced from one another by a distance of about $\frac{1}{16}$ to $\frac{1}{2}$ inch while the remote free ends of the first and second prongs 53, 53' are spaced from one another by a distance of about 0.110 inches or so, similar to the embodiment of FIGS. 13 and 13A.

The net result of this modification occurs during the dipping process or application of the polymeric material. That is, during the dipping process or application of the polymeric material, the remote free ends of the first and second prongs 53, 53' are located sufficiently closed to one another such that the plastisol at least partially fills the space or gap between the first and second prongs 53, 53' to form a web 89 therebetween, as well as encases and surrounds each one of the first and second prongs 53, 53' to thereby result in an integral mouthpiece comprising a pair of joined or interconnected mouthpieces 69, 69', once the first and second prongs 53, 53' are removed, which move in unison with one another. In all other respects, this embodiment is substantially identical to the embodiment of FIGS. 10A-10D, 11 and 11A. A through hole 93, which does not contain any plastisol, is formed in the cannula 60 and spaces the web 89 from the main body 71.

Figure 15:
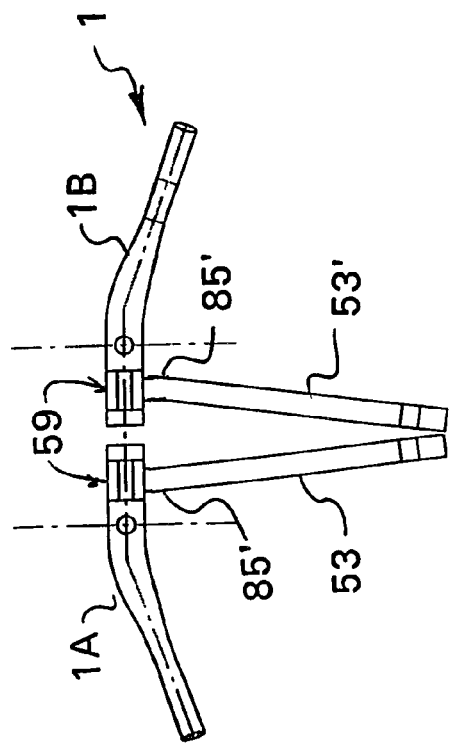
FIG. 15 a front view of yet another embodiment showing a partially assembled mandrel assembly having the pair of mouthpiece mandrels assembled with the pair of sections of the main body mandrel.

With reference to FIGS. 15 and 15A, a still further embodiment of the cannula mandrel assembly will now be discussed. For the sake of clarity, the nare mandrels are not shown attached respectively to the first or the second sections 1A, 1B of the main body forming mandrel 1 as seen in FIG. 15. As this embodiment is similar to the previous embodiments, identical reference numerals are given to identical elements and only the differences between this embodiment and the embodiment of FIGS. 10A-10D, in particular, will be discussed in detail.

The principal difference between this embodiment and the embodiment of FIGS. 10A-10D is that each one of the first and second prongs 53, 53' has a very gradual inclination or taper 85' toward one another, commencing adjacent the connecting end 59 of the respective first and second prongs 53, 53' and extending all the way to the free ends of the first and second prongs 53, 53'. As a result of very gradual inclination or taper toward one another, when the first and second prongs 53, 53' are engaged with the respective first and second sections 1A, 1B, the remote free ends of the first and second prongs 53, 53' are located in very close or possibly in abutting engagement or contact with one another. That is, the remote free ends of the first and second prongs 53, 53' are either in contact with one another or spaced from one another by a distance of less than 0.050 inches or so.

The net result of this modification occurs during the dipping process or application of the polymeric material. That is, during the dipping process or application of the polymeric material, the remote free ends of the first and second prongs 53, 53' are located sufficiently closed to one another such that the plastisol at least partially fills the space or gap between the first and second prongs 53, 53' to form a web 89 therebetween, as well as encases and surrounds each one of the first and second prongs 53, 53' to thereby result in an integral mouthpiece comprising a pair of joined or interconnected mouthpieces 69, 69' which, once the first and second prongs 53, 53' are removed, move in unison with one another. The opening for the two passageways 77, 79 is, in essence, a single common enlarged opening communicating with both passageways 77, 79. A through hole 93, which does not contain any plastisol, is formed in the cannula 60 and spaces the web 89 from the main body 71. In all other respect, this embodiment is substantially identical to the embodiment of FIGS. 10A-10D, 11 and 11A.

According to this application, the term "nasal cannula facepiece" generally comprises: (1) a hollow main body defining an internal chamber therein and having opposed first and second ends; and (2) at least one and preferably first and second nares which each communicate with the internal chamber of the main body and define respective first and second nare passages.

It is to be appreciated that the mouthpiece could also be injection molded as a single unitary piece or injection molded as two separate pieces, i.e., the facepiece separately molded from the mouthpiece, which are subsequently assembled with one another during a further manufacturing step. Alternatively, the cannula facepiece could also be either injection molded or formed by polymeric material which is cured. The cannula mouthpiece could be formed by injection molding, by a polymeric material which is cured, or extruded as a separate piece. The facepiece and the mouthpiece are subsequently assembled with one another to form a manufactured cannula.

The cannula, manufactured according to the present invention, is primary a divided cannula having two completely separate gas flow paths with each completely separate flow path communicating both with the nasal cavity, via one of the patient's nostrils, and the mouth or the oral cavity of the patient. Each one of the mouthpieces, for communicating with the mouth or the oral cavity of the patient, is molded with a sufficient curvature and of a sufficient length such that the free end of both mouthpieces will be typically located closely adjacent, or in direct contact with, the upper lip or lip region of the patient, depending upon the facial contour(s) of the patient. The curvatures of the mouthpieces in combination with the excess length of the mouthpieces results in extra length of the mouthpiece and facilitates trimming of an excess portion of the free of the mouthpiece so that the openings, for both mouthpieces, can be aligned substantially normal to the inhalation/exhalation path of the patient and thereby increase the sensitivity of the cannula.

Although the mouthpiece mandrel(s) is generally described as being attached to the main body mandrel by a centrally located slot which slidably engages or receives a rectangular section of the main body mandrel, it is to be appreciated that other types of releasable connections between those components could also be utilized, e.g., a pin received within a blind hole or blind recess, etc. The important aspect is that the mouthpiece mandrel(s) be adequately retained by the main body mandrel, during application of the polymeric material, while still being readily releasable from the main body mandrel, following curing of the cannula. The mouthpiece mandrel should also extends radially from and substantially perpendicular to the main body mandrel.

With reference to FIGS. 16A-16I, another embodiment of the cannula mandrel assembly will now be discussed. As this embodiment is somewhat similar to the first embodiment, identical reference numerals are given to identical elements and only the differences between this embodiment and the embodiment of FIGS. 1-8, in particular, will be discussed in detail.

Figure 16A:
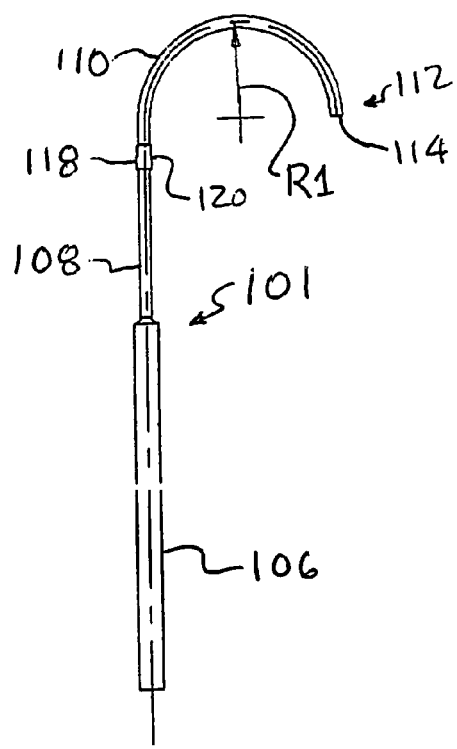
FIG. 16A is a diagrammatic side elevational view of a combined mouthpiece/nasal mandrel.
Figure 16C:
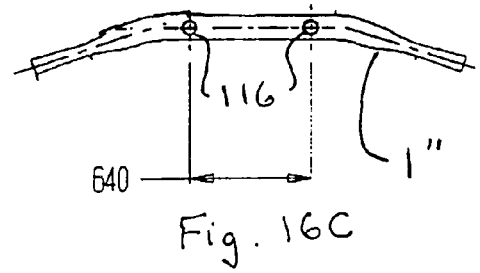
FIG. 16C is a diagrammatic top plan view of the facepiece mandrel of FIG. 16B.
Figure 16B:
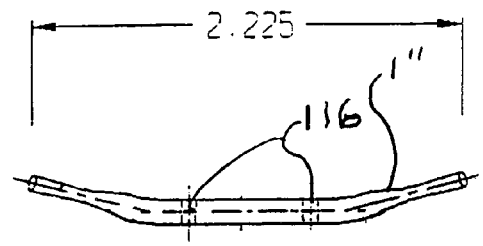
FIG. 16B is a diagrammatic front view of the facepiece mandrel.
Figure 16E:
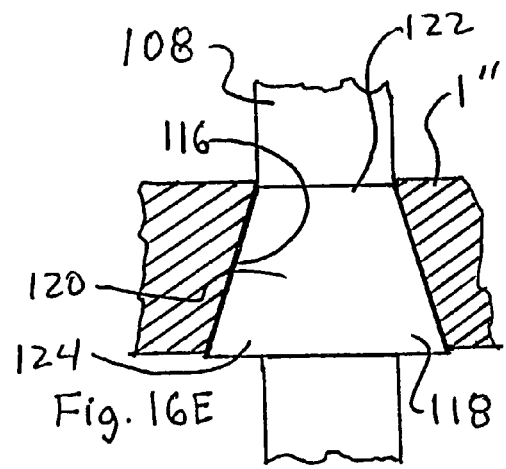
FIG. 16E is an enlarged diagrammatic view showing the intimate engagement between the tapering conical surface of the mouthpiece/nasal mandrel and the mating conical hole of the facepiece mandrel.
Figures 16F, 16G:
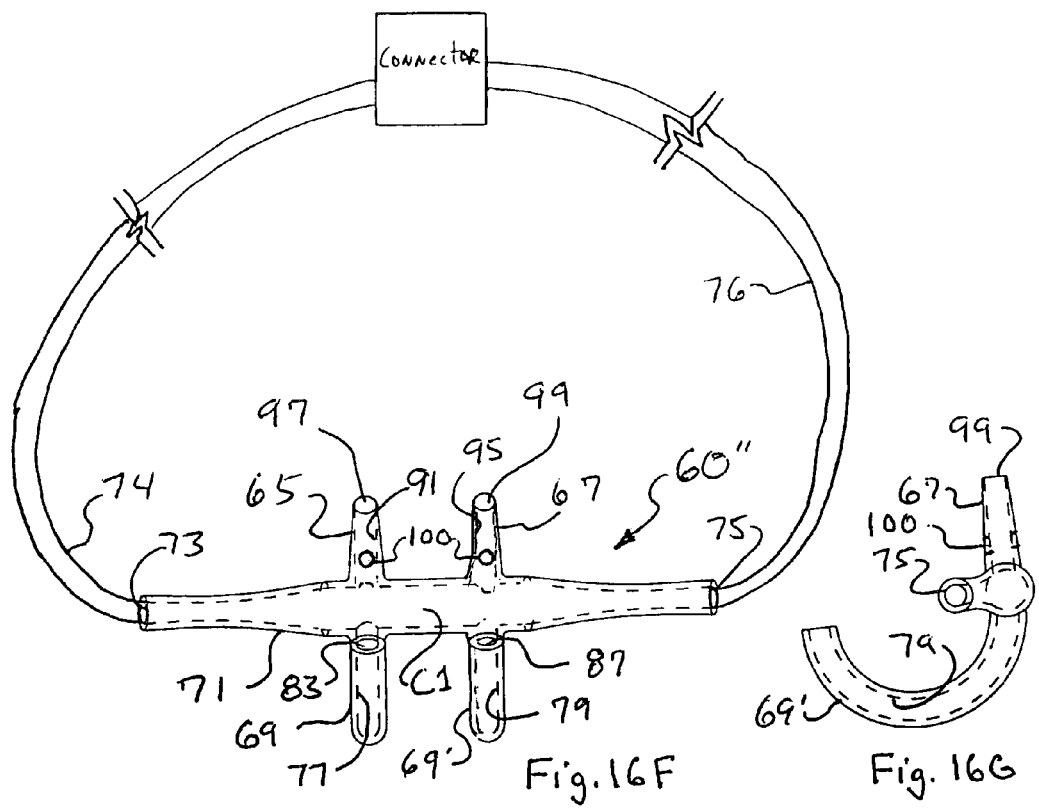
FIG. 16F is a diagrammatic front elevational view of a cannula, manufactured from the mandrel assembly of FIG. 16D, having a pair of separate mouthpieces with two nares and a single internal compartment or chamber.
FIG. 16G is a diagrammatic right side elevational view of a cannula of FIG. 16F.

As shown in FIG. 16D, this embodiment includes the cannula mandrel assembly 3" which has a pair of spaced apart mouthpiece/nasal mandrels 101 but this embodiment includes a continuous uninterrupted facepiece mandrel 1" (see FIGS. 16B and 16C), except for a pair of through holes, so that the manufactured cannula 60" is undivided (see FIGS. 16F and 16G). That is, the manufactured nasal cannula 60" has a single interior chamber or compartment C1 and that interior chamber or compartment C1 is in constant and continuous fluid communication with the formed passageways in the first and second nares and also with formed passageways in both of the first and the second mouthpieces 69, 69'.

The cannula mandrel assembly 3" is typically assembled on a molding base or platform 102, as can be seen in FIG. 16D. A first end of each of a pair of substantially identical mouthpiece/nasal mandrels 101 is inserted into a respective pair of spaced apart recess 104 formed in the molding base or platform 102. Each one of the mouthpiece/nasal mandrels 101 comprises a straight thickened base section 106 which extends substantially perpendicular to the molding base or platform 102. The thickened base section 106 transitions into a straight thinner base section 108 and the thickened and thinner base sections 106, 108 together have a combined length of at least an inch or so and preferably have a combined a length of about 1½ to about 2¼ inches or so. The thinner base section 108 then transitions into a curved section 110 generally having a radius of curvature R1 of between about 0.25 of an inch to about 1.5 inches or so, and more preferably a radius of curvature of between about 0.5 of an inch to about 0.75 inches or so. The radius of curvature R1 of the curved section 110 can vary, depending upon the cannula being manufactured, but is generally chosen to facilitate the alignment of an opening formed in the free end of the manufactured cannula mouthpiece with the opening of a mouth of the patient. The curved section 110 of the mouthpiece/nasal mandrels 101 forms the mouthpieces of the manufactured cannula 60". As can be seen in FIG. 16A, the free end 112 of each of mouthpiece/nasal mandrels 101 has a generally flat end wall 114. The end wall 114 of each of the nasal/mouthpiece/nasal mandrels 101 may be chamfered or otherwise contoured, e.g., tapered, rounded, pointed, etc., to facilitate receiving and engagement with a hole formed in the facepiece mandrel 1" and such engagement will be discussed below in further detail.

An intermediate section of the facepiece mandrel 1" is provided with a pair of spaced apart through holes 116 which are suitably spaced apart from one another and each is sized to receive a free leading end 112 of one of the mouthpiece/nasal mandrels 101 and facilitate mating engagement with the facepiece mandrel 1". The pair of holes 116, provided in the facepiece mandrel 1", must be sufficiently larger than the transverse cross sectional area or dimension of the mouthpiece/nasal mandrels 101 to allow each hole 116 of the facepiece mandrel 1" to receive a respective free leading end 112 of one of the mouthpiece/nasal mandrels 101 and also allow the facepiece mandrel 1" to slide along the curved section 110 and the thinner base section 108 of both of the mouthpiece/nasal mandrels 101 until the facepiece mandrel 1" abuts against a stop feature or element 118 provided in the thinner base section 108 adjacent the transition between the thinner base section 108 and the curved section 110 (see FIGS. 16A and 16D). The stop feature or element 118 is an interference expansion which prevents further sliding movement of the facepiece mandrel 1" along the respective the mouthpiece/nasal mandrels 101 toward the molding base or platform 102. It is desirable for the free ends 112 of the mouthpiece/nasal mandrels 101 to be spaced apart from one another by a distance slightly larger than the spacing of the pair of through holes 116 in the facepiece mandrel 1". That is, the spaced apart recess 104, formed in the molding base or platform 102, can be spaced slightly further apart than the hole to hole spacing in the facepiece mandrel 1" or mouthpiece/nasal mandrels 101 can bow or flare slightly away for one another adjacent the respective free leading ends 112. Such spacing results in a sliding friction between the inner surface of the holes 116 in the facepiece mandrel 1" and the exterior surface of the mouthpiece/nasal mandrels 101 and further assists with retaining the facepiece mandrel 1" in its finally installed position, i.e., engaged with the stop feature or element 118. The friction, between the facepiece mandrel 1" and the mouthpiece/nasal mandrels 101, ensures that the facepiece mandrel 1" does not become inadvertently disengaged from the stop feature or element 118 during manufacture or molding of the cannula, especially during the dipping process.

According to this embodiment, the stop feature or element 118 is a thickened region area or region in the thinner base section 108 but adjacent the transition between the thinner base section 108 and the curved section 110. Preferably, this thickened area or region is conically shaped and the two holes 116, provided in the facepiece mandrel 1", have a mating conically shaped hole 116 which facilitates an intimate mating engagement between the these conically shaped surfaces so as to provide an intimate locking engagement therebetween and facilitate retaining the facepiece mandrel 1" in engagement with the stop feature or element 118 of the mouthpiece/nasal mandrels 101 even when the cannula mandrel assembly 3" is flipped over or otherwise manipulated during manufacture of the cannula.

Both the thinner base section 108 and the curved section 110 have a substantially constant transverse cross sectional diameter or dimension of about 0.062 inches along their length. The holes 116 of the facepiece mandrel 1" each have a transverse cross sectional diameter or dimension which is slightly larger than the transverse cross sectional diameter or dimension of the mouthpiece/nasal mandrels 101, e.g., larger than the transverse cross sectional dimension or diameter of the thinner base and curved sections 108, 110 by between about 0.070 inches or so. The larger diameter or dimension of the holes 116 facilitate sliding movement of the facepiece mandrel 1", along the exterior surface of the mouthpiece/nasal mandrels 101, and also allow the facepiece mandrel 1" to slide relatively freely around the curved section 110 of the mouthpiece/nasal mandrels 101. It is to be appreciated that the space or gap, formed between the inwardly facing surface of the holes 116 of the facepiece mandrel 1" and the exterior surface of the mouthpiece/nasal mandrels 101 once the facepiece mandrel 1" abuts against the stop features or elements 118, must be sufficiently small so as to avoid a significant amount of the plastisol or plastics material from "flashing" or flowing in any space or gap between the facepiece and mouthpiece/nasal mandrels. It is to be appreciated that the transverse cross sectional diameter or dimension of the mouthpiece/nasal mandrels 101 can vary, i.e., can be other than circular, depending upon the particular application.

As shown in the drawings, the stop feature or element 118 is a tapering conical section (see FIG. 16E) which is formed integrally with the thinner base section 108 at a location adjacent the transition of the thinner base section 108 into the curved section 110. The tapering conical section 120 has a smaller dimensioned end 122, located remote from the molding base or platform 102, with a diameter of about 0.070 inches or so while the larger dimensioned end 124 of the tapering conical section, located closest to the molding base or platform 102, has a diameter of about 0.078 inches or so. The mating tapers, between the holes 116 of the facepiece mandrel 1" and the tapering conical section 120 of the thinner base section 108 of the mouthpiece/nasal mandrels 101, provide an intimate contact between the mating conical surfaces of these two components which avoids or minimizes formation of any gaps or spaces therebetween and thus minimizes any "flashing" or the flow of the plastisol or plastics material between the main and mouthpiece/nasal mandrels 101 during manufacture of the cannula.

It is to be appreciated that although the stop feature or element 118 is described as a tapering conical section 120 and a mating conical hole 116 in the facepiece mandrel 1", other complimentary mating arrangements, which both facilitate retaining the facepiece mandrel 1" in position while also minimizing the flow of the plastisol or plastics material between the facepiece mandrel 1" and the mouthpiece/nasal mandrels 101 during manufacture of the cannula, would be readily apparent to those skilled in the art and are considered to be within the spirit and scope of this invention.

Due to the fact that the mouthpiece/nasal mandrels 101 is a single mandrel, this results in the first nare 65 being aligned and coincident with the associated first mouthpiece 69 and the second nare 67 being aligned and coincident with the associated second mouthpiece 69'.

Following molding of the cannula, according to the process described above, the facepiece mandrel 1", along with the manufactured cannula 60", is disengaged from its intimate locking engagement with the pair of stop feature or elements 118 of mouthpiece/nasal mandrels 101 by sliding these components along both of the mouthpiece/nasal mandrels 101 toward the free ends 112 until both the facepiece mandrel 1" and the manufactured cannula 60" disengaged from the free ends 112 and are completely removed from both of the mouthpiece/nasal mandrels 101. Next, the facepiece mandrel 1" is then extracted or removed from the manufactured cannula 60" by pulling one end of the facepiece mandrel 1" away from the manufactured cannula 60", via one of the opposed end openings 73 or 75, until the facepiece mandrel 1" is completely separated and removed from the manufactured cannula 60" thereby forming the manufactured cannula 60'''.

With reference to FIGS. 16F and 16G, the cannula 60", manufactured by the cannula mandrel assembly 3" of this embodiment, will now be discussed. The manufactured cannula 60", formed from the above described process and cannula mandrel assembly 3" shown in FIG. 16D, comprises a main body 71 with a single internal chamber having end opposed openings 73, 75 which are coupled by an adhesive, such as MEK for example, to one end of a flexible gas delivery, pressure detecting or gas sampling tubing or conduit 74, 76. The opposite end of the sampling tubing or conduit 74, 76 is typically connected to a conventional connector (only diagrammatically shown) which facilitates connection to a desired device, such as a gas delivery device, a pressure detecting device, a gas sampling device, etc. The internal compartment C1 communicates with the first end opening 73, a first fluid passageway 91 formed in the first nare 65 and with a first fluid passageway 77 formed in the first mouthpiece 69, while the internal compartment C1 also communicates with the second end opening 75, a second fluid passageway 95 formed in the second nare 67 and with a second fluid passageway 79 formed in the second mouthpiece 69'. The first fluid passageway 91 communicates with a primary aperture (inlet/outlet) 97 formed in end surface of the first nare 65 while the second fluid passageway 95 communicates with a primary aperture (inlet/outlet) 99 formed in end surface of the second nare 67. The first fluid passageway 77 communicates with an inlet/outlet aperture 83 formed in end surface of the first mouthpiece 69 while the second fluid passageway 79 communicates with an inlet/outlet aperture 87 formed in end surface of the first mouthpiece 69'. The pair of centrally located but spaced apart nares 65, 67 are located on the cannula 60" for insertion into the nostrils of a patient's nose while the first and second centrally located mouthpieces 69, 69' are both located adjacent the middle section of the main body 71 for insertion or communication with the mouth of the patient.

Figures 16H, 16I:
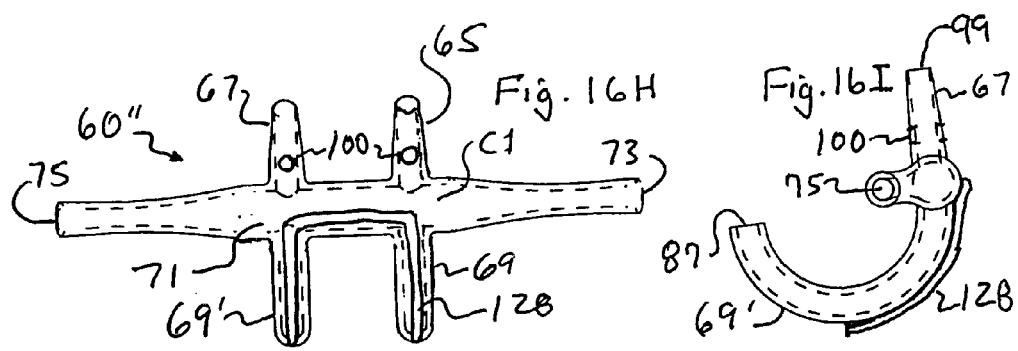
FIG. 16H is a diagrammatic rear elevational view of a cannula, manufactured from the mandrel assembly of FIG. 16D, having a pair of separate mouthpieces with two nares, a single internal compartment or chamber and a reinforcing wire.
FIG. 16I is a diagrammatic left side elevational view of a cannula of FIG. 16G.

With reference to FIG. 16H, if desired, the cannula 60 of FIG. 16F can be provided with a wire 128 to facilitate alignment and retention of the mouthpieces in aligned positions during use of the cannula. To achieve this, a first end of the wire 128 is glued or otherwise permanently affixed to an intermediate region of a top surface of the first mouthpiece 69 and the wire 128 then extends along the mouthpiece toward the main body 71 of the cannula 60". The wire 128 bends 90 degrees and then extends along a top surface of the main body 71 toward the second mouthpiece 69' and then again bends 90 degrees and, thereafter, extends along the top surface of the second mouthpiece 69' and terminates in a second end at an intermediate location along the second mouthpiece 69'. Preferably the wire 128 is glued or otherwise permanently secured to the cannula along its entire length so that the wire 128 does not become separated or dislodged from the cannula 60". The wire 128 typically has a diameter of between 0.01 and 0.2 inches or so.

Following manufacture of the cannula 60", at least one and possibly both of the spaced apart first and second nares 65, 67 is provided with a secondary aperture 100, along an intermediate length of the nare, to provide a secondary inlet/outlet of the nare 65, 67 depending upon the function of the cannula 60", which facilitates, via the secondary inlet/outlet, delivery of a supply gas to the respective nare, monitoring or sampling of a gas from the associated nostril of a patient, etc., in the event that the primary aperture (inlet/outlet) 97 or 99 of the respective nares 65, 67 becomes obstructed, clogged or occluded for some reason, e.g., mucosal secretions and/or soft nasal tissue is sucked into the primary aperture 97 and/or 99 and thus becomes partially or completely blocked, covered or obstructed thereby, etc. The secondary apertures 100 to be formed in the nare 65 and/or 67 are sized to be smaller than the primary aperture (inlet/outlet) 97 and 99 formed in the end of each nare 65, 67 but sufficiently large to function, e.g., supplying a treating gas to a patient, withdraw or sample an exhalation gas(es) from the patient, monitor breathing characteristics, detect pressure, etc. That is, the secondary aperture (inlet/outlet) 100 of the nare 65, 67 allows the nare to still function in the event that the primary aperture (inlet/outlet) 97 or 99 becomes obstructed, clogged or occluded for some reason during use of the cannula so that the nare may still function. The secondary aperture 100 preferably has a diameter of between 0.05 and 0.07 inches. For ease of manufacture, the secondary aperture 100 extends through both opposed side walls of the nare 65, 67 to form two opposed and identical secondary apertures 100 in the nares 65, 67, but two secondary apertures 100 is not required.

Since certain changes may be made in the above described improved cannula and method of manufacturing the same, without departing from the spirit and scope of the invention herein involved, it is intended that all of the subject matter of the above description or shown in the accompanying drawings shall be interpreted merely as examples illustrating the inventive concept herein and shall not be construed as limiting the invention.

We claim:

1. A method of forming a cannula comprising the steps of:
   assembling a cannula mandrel assembly comprising separable engageable parts including a facepiece mandrel and a pair of mouthpiece/nasal mandrels, an intermediate section of the facepiece mandrel being provided with a pair of spaced apart through holes for each receiving a remote free end of one of the mouthpiece/nasal mandrels and allowing the facepiece mandrel to slide along the pair of mouthpiece/nasal mandrels, and each of the mouthpiece/nasal mandrels having a stop feature, with a larger transverse cross section, which prevents further sliding movement of the facepiece mandrel along the pair of mouthpiece/nasal mandrels and while also avoiding flow of a polymeric material between the facepiece mandrel and the mouthpiece/nasal mandrels;
   heating the cannula mandrel assembly to a desired temperature;
   providing an uncured polymeric material in flowable state;
   applying at least one coating of the uncured polymeric material to the cannula mandrel assembly to provide a desired material thickness coating on the cannula mandrel assembly;
   at least partially curing the coating of the polymeric material on the cannula mandrel assembly to form the cannula;
   disassembling the cannula mandrel assembly by first sliding both the facepiece mandrel and the formed cannula along the mouthpiece/nasal mandrels toward the remote free ends of the mouthpiece/nasal mandrels until the facepiece mandrel and the partially cured cannula are completely removed from the pair of mouthpiece/nasal mandrels; and then withdrawing the facepiece mandrel from the formed cannula.

2. The method according to claim 1, further comprising the steps of forming the stop feature as a thickened area on each of the mouthpiece/nasal mandrels, and providing the through holes of the facepiece mandrel with a mating complimentary feature which intimately engages with the thickened area of the mouthpiece/nasal mandrels to retain the facepiece mandrel in engagement with the stop feature during manufacture of the cannula and avoid flow of the polymeric material between the facepiece mandrel and the mouthpiece/nasal mandrels.

3. The method according to claim 2, further comprising the steps of using a tapering conical section as the thickened area on each of the mouthpiece/nasal mandrels, and providing tapering conical holes in the facepiece mandrel as the mating complimentary feature which intimately engage with one another to retain the facepiece mandrel in engagement with the stop feature during manufacture of the cannula.

4. The method according to claim 2, further comprising the step of inserting a first end of each of the pair of mouthpiece/nasal mandrels into a respective spaced apart recesses formed in a molding base such that the pair of mouthpiece/nasal mandrels are retained and supported by and extend substantially perpendicular to the molding base.

5. The method according to claim polymeric material 4, further comprising the steps of forming the tapering conical section of each mouthpiece/nasal mandrels with a smaller dimensioned end, located remote from the molding base, with a diameter of about 0.070 inches while a larger dimensioned end of the tapering conical section, located closest to the molding base, has a diameter of about 0.078 inches.

6. The method according to claim 3, further comprising the step of forming each one of the mouthpiece/nasal mandrels as a straight base section which transitions into a curved section.

7. The method according to claim 6, further comprising the step of providing the curved section of each mouthpiece/nasal mandrel with a radius of curvature of between about 0.25 of an inch to about 1.5 inches.

8. The method according to claim 1, further comprising the step of contouring the remote free end of each of the mouthpiece/nasal mandrels to facilitate receiving and engagement with the holes of the facepiece mandrel.

9. The method according to claim 1, further comprising the step of manufacturing the cannula mandrel assembly from beryllium copper.

10. The method according to claim 1, further comprising the step of coating the cannula mandrel assembly with a layer of release material prior to applying the at least one coating of the polymeric material thereto.

11. The method according to claim 1, further comprising the steps of heating the cannula mandrel assembly at a temperature of from about 350° F. to about 550° F. prior applying the polymeric material to the cannula mandrel assembly; and
forming at least one secondary aperture in a sidewall of at least one of the nares.

12. The method according to claim 1, further comprising the step of applying the polymeric material to the cannula mandrel assembly by at least one dipping step during a dipping process.

13. The method according to claim 1, further comprising the step of curing the polymeric material by heating the polymeric material at a temperature of from about 410° F. to about 450° F.

14. The method according to claim 1, further comprising the step of partially curing the polymeric material using heat from the heated cannula mandrel assembly and further curing of the polymeric material in an oven.

15. The method according to claim 1, further comprising the step of spacing the remote free ends of the mouthpiece/nasal mandrels from one another by a distance greater than a spacing of the pair of holes in the facepiece mandrel such that a sliding friction occurs between an inner surface of the holes in the facepiece mandrel and an exterior surface of the mouthpiece/nasal mandrels to assist with retaining the facepiece mandrel in engagement with the stop features.

16. The method according to claim 1, further comprising the step of forming the holes in the facepiece mandrel to have a transverse cross sectional dimension which is greater than, by about 0.070 of an inch, a transverse cross sectional dimension of the mouthpiece/nasal mandrels; and
affixing a wire to at least a portion of first and second mouthpieces to facilitate adjustable retention of the mouthpieces in aligned positions during use of the cannula.

17. A nasal and oral cannula having a pair of nares and a pair of mouthpieces with a contiguous flow path between the pair of nares and the pair of mouthpieces, the nasal and oral cannula manufactured by the method comprising the steps of:
assembling a cannula mandrel assembly comprising separable engageable parts including a facepiece mandrel and a pair of mouthpiece/nasal mandrels, an intermediate section of the facepiece mandrel being provided with a pair of spaced apart conical through holes for each receiving a remote free end of one of the mouthpiece/nasal mandrels and allowing the facepiece mandrel to slide along the pair of mouthpiece/nasal mandrels, and each of the mouthpiece/nasal mandrels having a tapering conical section which forms a stop which prevents further sliding movement of the facepiece mandrel along the pair of mouthpiece/nasal mandrels and while also avoiding flow of a polymeric material between the facepiece mandrel and the mouthpiece/nasal mandrels;
heating the cannula mandrel assembly to a desired temperature;
providing an uncured polymeric material in flowable state;
applying at least one coating of the polymeric material to the cannula mandrel assembly to provide a desired material thickness coating on the cannula mandrel assembly;
at least partially curing the coating of the polymeric material on the cannula mandrel assembly to form the cannula;
disassembling the cannula mandrel assembly by first sliding both the facepiece mandrel and the formed cannula along the mouthpiece/nasal mandrels toward the remote free ends of the mouthpiece/nasal mandrels until the facepiece mandrel and the partially cured cannula are completely removed from the pair of mouthpiece/nasal mandrels; and then withdrawing the facepiece mandrel from the formed cannula.

18. A nasal and oral cannula having a first and second nares and first and second curved mouthpieces with a contiguous flow path between the first and second nares and the first and second curved mouthpieces, the nasal and oral cannula comprising:
a main body having opposed end openings and defining a single internal compartment;
the first nare, for insertion into a nostril of a patient, being coupled to the main body and communicating with the internal compartment, and the first nare having an inlet/outlet opening at a free end thereof;
the second nare, for insertion into a second nostril of the patient and spaced from the first nare, being coupled to the main body and communicating with the internal compartment, and the second nare having an inlet/outlet opening at a free end thereof;
the first curved mouthpiece being coupled to the main body and communicating with the internal compartment, and the first curved mouthpiece having an inlet/outlet opening at a free end thereof;

the second curved mouthpiece, spaced from the first curved mouthpiece, being coupled to the main body and communicating with the internal compartment, and the second curved mouthpiece having an inlet/outlet opening at a free end thereof; and the curvature of the first and second curved mouthpieces in combination with an excess length of the first and second curved mouthpieces results in extra length of the first and second curved mouthpiece and facilitates trimming of an excess portion of free ends of the first and second curved mouthpieces so that the openings, of both the first and second curved mouthpieces, can be aligned substantially normal to an inhalation/exhalation path of the patient and thereby increase the sensitivity of the cannula.

19. The nasal and oral cannula according to claim 18, wherein a wire is affixed to at least a portion of the first and second curved mouthpieces to facilitate adjustable retention of the first and second curved mouthpieces during use of the nasal and oral cannula.

20. The nasal and oral cannula according to claim 18, wherein at least one secondary aperture is formed in a sidewall of at least one of the nares.

* * * * *